(12) United States Patent
Davis et al.

(10) Patent No.: US 8,871,912 B2
(45) Date of Patent: Oct. 28, 2014

(54) ENGINEERED HETERODIMERIC PROTEIN DOMAINS

(75) Inventors: Jonathan H. Davis, Auburndale, MA (US); James S. Huston, Newton Lower Falls, MA (US)

(73) Assignee: Merck Patent GmbH, Darmstadt (DE)

( * ) Notice: Subject to any disclaimer, the term of this patent is extended or adjusted under 35 U.S.C. 154(b) by 1751 days.

(21) Appl. No.: 11/728,048

(22) Filed: Mar. 23, 2007

(65) Prior Publication Data

US 2007/0287170 A1 Dec. 13, 2007

Related U.S. Application Data

(60) Provisional application No. 60/785,474, filed on Mar. 24, 2006.

(51) Int. Cl.
*C12P 21/08* (2006.01)
*C07K 16/00* (2006.01)
*C07K 16/46* (2006.01)
*C07K 16/24* (2006.01)

(52) U.S. Cl.
CPC ............... *C07K 16/00* (2013.01); *C07K 16/468* (2013.01); *C07K 2317/21* (2013.01); *C07K 2319/30* (2013.01); *C07K 2317/52* (2013.01); *C07K 2319/00* (2013.01); *C07K 16/246* (2013.01)
USPC ..................................................... 530/387.3

(58) Field of Classification Search
USPC .................................. 530/350, 387.1, 387.3
See application file for complete search history.

(56) References Cited

U.S. PATENT DOCUMENTS

| | | | |
|---|---|---|---|
| 5,258,498 A | 11/1993 | Huston et al. | |
| 5,482,858 A | 1/1996 | Huston et al. | |
| 5,731,168 A * | 3/1998 | Carter et al. | 435/69.1 |
| 5,807,706 A | 9/1998 | Carter et al. | |
| 5,856,456 A | 1/1999 | Whitlow et al. | |
| 5,990,275 A | 11/1999 | Whitlow et al. | |
| 6,472,179 B2 | 10/2002 | Stahl et al. | |
| 6,969,517 B2 | 11/2005 | Gillies et al. | |
| 2002/0062010 A1 | 5/2002 | Arathoon et al. | |
| 2002/0155537 A1* | 10/2002 | Carter et al. | 435/69.1 |
| 2005/0249723 A1* | 11/2005 | Lazar | 424/133.1 |

FOREIGN PATENT DOCUMENTS

| | | |
|---|---|---|
| WO | WO-0100814 | 1/2001 |
| WO | WO-03012069 | 3/2003 |

OTHER PUBLICATIONS

Dixon (Proteins. 1997; Suppl 1: 198-204).*
Lensink et al. (Proteins. 2007; 69: 704-718).*
Kostelny et al (J. Imm., 148:1547-1553, 1992).*
Ridgway et al (Prot. Eng., 9:617-621, 1996).*
Arakawa et al. (1994) "Formation of heterodimers from three neurotrophins, nerve growth factor, neurotrophin-3, and brain-derived neurotrophic factor," J. Biol. Chem. 269(45):27833-27839.
Arndt et al. (2000) "A Heterodimeric Coiled-coil Peptide Pair Selected in Vivo from a Designed Library-Versus-Library Ensemble," Journal of Molecular Biology 295(3):627-639.
Fanger et al. (1992) Crit. Rev. Immunol. 12:101-124.
Graddis et al. (1993) "Controlled Formation of Model Homo- and Heterodimer Coiled Coil Polypeptidases," Biochemistry 32(47):12664-12671.
Lo et al. (1998) "High level expression and secretion of Fc-X fusion proteins in mammalian cells." Protein Engineering 11:495.
Martin et al. (2001) "Crystal structure at 2.8 A of an FcRn/ heterodimeric Fc complex: mechanism of pH-dependent binding," Molec. Cell 7:867.
Radziejewski et al. (1993) "Heterodimers of the neurotrophic factors: formation, isolation, and differential stability," Biochem. 32(48):13350.
Singh et al. (2001) "Simultaneous estimation of geniposide and genipin in mouse plasma using high-performance liquid chromatography," Bioinformatics 17:1236-1237.
Sturniolo et al. (1999) "Generation of tissue-specific and promiscuous HLA ligand databases using DNA microarrays and virtual HLA class II matrices," Nature Biotechnol. 17:555-561.

* cited by examiner

*Primary Examiner* — Brad Duffy
(74) *Attorney, Agent, or Firm* — Goodwin Procter LLP

(57) ABSTRACT

The present invention provides an engineered multidomain protein including at least two nonidentical engineered domains, each of which contains a protein-protein interaction interface containing amino acid sequence segments derived from two or more existing homologous parent domains, thereby conferring on the engineered domains assembly specificities distinct from assembly specificities of the parent domains. In particular, the engineered domains form heterodimers with one another preferentially over forming homodimers. Methods of designing and using the engineered proteins are also included.

5 Claims, 16 Drawing Sheets

A  C  D

F  G  H  I

```
                3           3           3           3           3
                4           5           6           7           8
                1           0           0           0           0
Hu_IgG:    GQPREPQVYTLPPSREEM-TKNQVSLTCLVKGFYPSDIAVEWESNGQPEN
                ♦ ♦ ♦♦ ♦ ♦♦  ♦♦ ♦ ♦ ♦♦ ♦ ♦
Hu_IgA:    GNTFRPEVHLLPPPSEELALNELVTLTCLARGFSPKDVLVRWLQGSQELP
           3         3         3         3         3         3
           4         5         6         7         8         9
           2         0         0         0         0         0

3           4           4           4           4
             9           0           1           2           3
             0           0           0           0           0
Hu_IgG:    --NYKTTPPVLDSD---GSFFLYSKLTVDKSRWQQGNVFSCSVMHEALHN
             ♦ ♦ ♦♦ ♦ ♦♦      ♦ ♦ ♦ ♦
Hu_IgA:    REKYLTWASRQEPSQGTTTFAVTSILRVAAEDWKKGDTFSCMVGHEALPL
                     4         4         4         4         4
                     0         1         2         3         4
                     0         0         0         0         0

4
           4
           0
Hu_IgG:    HYTQKSLSL
                ♦
Hu_IgA:    AFTQKTIDR
                4
                5
                0
```

Figure 2

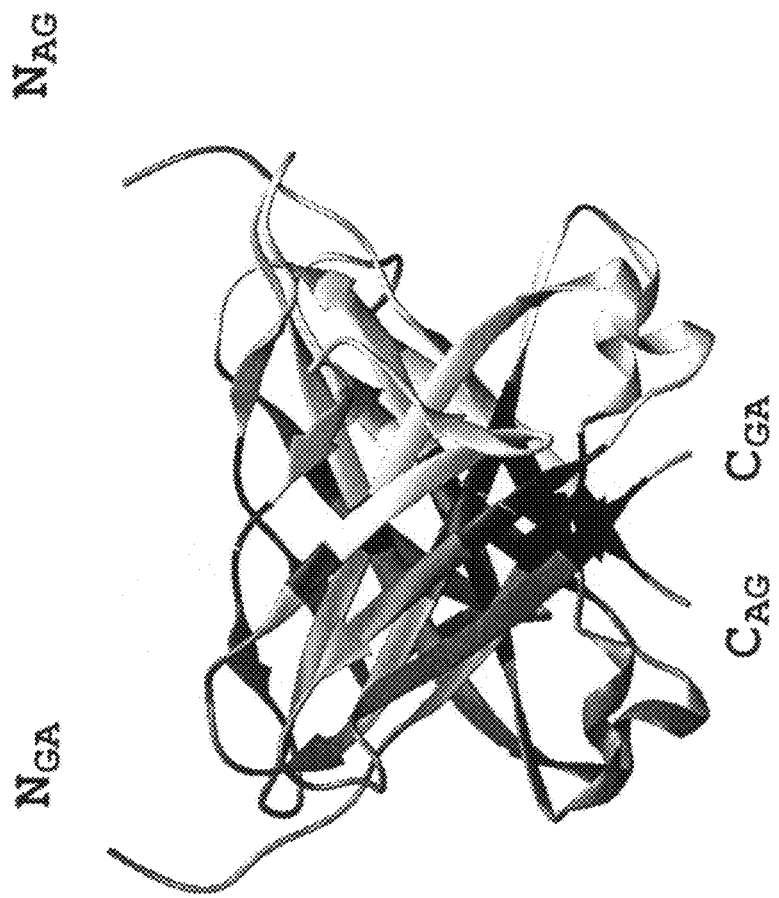

A.

B.

A.

B.

C.

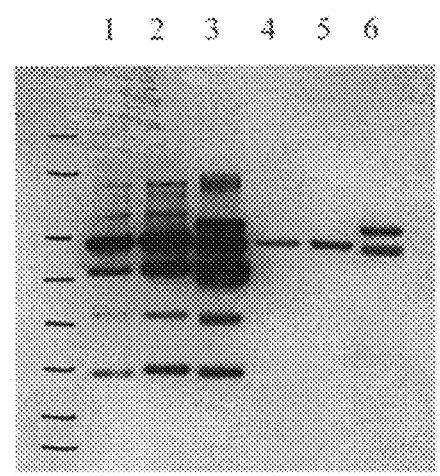
FIG. 12D Western Blot Non-reduced Gel
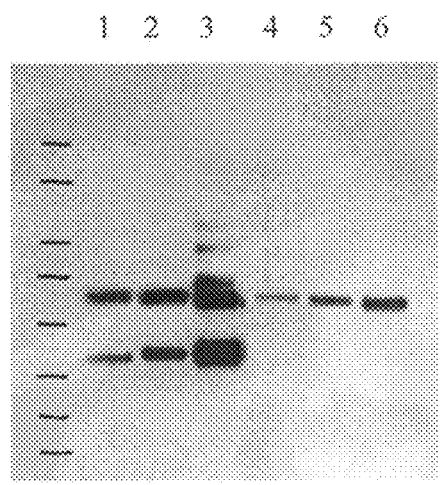
FIG. 12E Western Blot Reduced Gel

SEQUENCE LISTING

<160> NUMBER OF SEQ ID NOS: 54

<210> SEQ ID NO 1
<211> LENGTH: 106
<212> TYPE: PRT
<213> ORGANISM: Artificial sequence
<220> FEATURE:
<223> OTHER INFORMATION: Polypeptide sequence of AG SEED, with variant
      amino acids
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (103)..(103)
<223> OTHER INFORMATION: Xaa is any amino acid

<400> SEQUENCE: 1

Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
            20                  25                  30

Tyr Pro Xaa Asp Ile Ala Val Glu Trp Glu Ser Asn Gly Gln Pro Glu
        35                  40                  45

Asn Asn Tyr Lys Thr Thr Pro Ser Arg Gln Glu Pro Ser Gln Gly Thr
    50                  55                  60

Thr Thr Phe Ala Val Thr Ser Lys Leu Thr Xaa Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Xaa Ile Ser Leu
            100                 105

<210> SEQ ID NO 2
<211> LENGTH: 106
<212> TYPE: PRT
<213> ORGANISM: Artificial sequence
<220> FEATURE:
<223> OTHER INFORMATION: Polypeptide sequence of GA SEED, with variant
      amino acids
<220> FEATURE:
<221> NAME/KEY: MISC_FEATURE
<222> LOCATION: (23)..(23)
<223> OTHER INFORMATION: Xaa is any amino acid
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (61)..(61)
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid

<400> SEQUENCE: 2

Gly Gln Pro Arg Glu Pro Gln Val Tyr Thr Leu Pro Pro Ser Glu
1               5                   10                  15

Glu Leu Ala Leu Asn Glu Xaa Val Thr Leu Thr Cys Leu Val Lys Gly
            20                  25                  30

Phe Tyr Pro Ser Asp Ile Ala Val Glu Trp Leu Gln Gly Ser Gln Glu
        35                  40                  45

Leu Pro Arg Glu Lys Tyr Leu Thr Trp Xaa Pro Val Xaa Asp Ser Asp
    50                  55                  60

Gly Ser Xaa Phe Leu Tyr Ser Ile Leu Arg Val Xaa Ala Xaa Asp Trp
65                  70                  75                  80

Lys Lys Gly Asp Thr Phe Ser Cys Ser Val Met His Glu Ala Leu His
                85                  90                  95

Asn His Tyr Thr Gln Lys Ser Leu Asp Arg
            100                 105

<210> SEQ ID NO 3
<211> LENGTH: 106
<212> TYPE: PRT
<213> ORGANISM: Artificial sequence
<220> FEATURE:
<223> OTHER INFORMATION: Polypeptide sequence of AG(f0) SEED

<400> SEQUENCE: 3

Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
            20                  25                  30

Tyr Pro Lys Asp Ile Ala Val Glu Trp Glu Ser Asn Gly Gln Pro Glu
        35                  40                  45

Asn Asn Tyr Lys Thr Thr Pro Ser Arg Gln Glu Pro Ser Gln Gly Thr
    50                  55                  60

Thr Thr Phe Ala Val Thr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Thr Ile Ser Leu
            100                 105

<210> SEQ ID NO 4
<211> LENGTH: 106
<212> TYPE: PRT
<213> ORGANISM: Artificial sequence
<220> FEATURE:
<223> OTHER INFORMATION: Polypeptide sequence of AG(f1) SEED

<400> SEQUENCE: 4

Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Ser Arg Gln Glu Pro Ser Gln Gly Thr
    50                  55                  60

Thr Thr Phe Ala Val Thr Ser Lys Leu Thr Val Asp Lys Ser Arg Trp
65                  70                  75                  80

```
Gln Gln Gly Asn Val Phe Ser Cys Ser Val Met His Glu Ala Leu His
                85                  90                  95

Asn His Tyr Thr Gln Lys Ser Ile Ser Leu
            100                 105
```

<210> SEQ ID NO 5
<211> LENGTH: 106
<212> TYPE: PRT
<213> ORGANISM: Artificial sequence
<220> FEATURE:
<223> OTHER INFORMATION: Polypeptide sequence of AG(f2) SEED

<400> SEQUENCE: 5

```
Gly Gln Pro Phe Arg Pro Glu Val His Leu Leu Pro Pro Ser Arg Glu
1               5                   10                  15

Glu Met Thr Lys Asn Gln Val Ser Leu Thr Cys Leu Ala Arg Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Ser Arg Gln Glu Pro Ser Gln Gly Thr
    50                  55                  60

Thr Thr Phe Ala Val Thr Ser Lys Leu Thr Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Ile Ser Leu
            100                 105
```

<210> SEQ ID NO 6
<211> LENGTH: 106
<212> TYPE: PRT
<213> ORGANISM: Artificial sequence
<220> FEATURE:
<223> OTHER INFORMATION: Polypeptide sequence of GA(f0) SEED

<400> SEQUENCE: 6

```
Gly Gln Pro Arg Glu Pro Gln Val Tyr Thr Leu Pro Pro Ser Glu
1               5                   10                  15

Glu Leu Ala Leu Asn Glu Leu Val Thr Leu Thr Cys Leu Val Lys Gly
                20                  25                  30

Phe Tyr Pro Ser Asp Ile Ala Val Glu Trp Leu Gln Gly Ser Gln Glu
            35                  40                  45

Leu Pro Arg Glu Lys Tyr Leu Thr Trp Ala Pro Val Leu Asp Ser Asp
    50                  55                  60

Gly Ser Phe Phe Leu Tyr Ser Ile Leu Arg Val Ala Ala Glu Asp Trp
65                  70                  75                  80

Lys Lys Gly Asp Thr Phe Ser Cys Ser Val Met His Glu Ala Leu His
                85                  90                  95

Asn His Tyr Thr Gln Lys Ser Leu Asp Arg
            100                 105
```

<210> SEQ ID NO 7
<211> LENGTH: 106
<212> TYPE: PRT
<213> ORGANISM: Artificial sequence
<220> FEATURE:
<223> OTHER INFORMATION: Polypeptide sequence of GA(f1) SEED

```
<400> SEQUENCE: 7

Gly Gln Pro Arg Glu Pro Gln Val Tyr Thr Leu Pro Pro Ser Glu
1               5                   10                  15

Glu Leu Ala Leu Asn Glu Gln Val Thr Leu Thr Cys Leu Val Lys Gly
            20                  25                  30

Phe Tyr Pro Ser Asp Ile Ala Val Glu Trp Leu Gln Gly Ser Gln Glu
        35                  40                  45

Leu Pro Arg Glu Lys Tyr Leu Thr Trp Thr Pro Val Val Asp Ser Asp
    50                  55                  60

Gly Ser Phe Phe Leu Tyr Ser Ile Leu Arg Val Thr Ala Asp Asp Trp
65                  70                  75                  80

Lys Lys Gly Asp Thr Phe Ser Cys Ser Val Met His Glu Ala Leu His
                85                  90                  95

Asn His Tyr Thr Gln Lys Ser Leu Asp Arg
            100                 105

<210> SEQ ID NO 8
<211> LENGTH: 106
<212> TYPE: PRT
<213> ORGANISM: Artificial sequence
<220> FEATURE:
<223> OTHER INFORMATION: Polypeptide sequence of GA(f2) SEED

<400> SEQUENCE: 8

Gly Gln Pro Arg Glu Pro Gln Val Tyr Thr Leu Pro Pro Ser Glu
1               5                   10                  15

Glu Leu Ala Leu Asn Glu Gln Val Thr Leu Thr Cys Leu Val Lys Gly
            20                  25                  30

Phe Tyr Pro Ser Asp Ile Ala Val Glu Trp Leu Gln Gly Ser Gln Glu
        35                  40                  45

Leu Pro Arg Glu Lys Tyr Leu Thr Trp Ala Pro Val Asp Asp Ser Asp
    50                  55                  60

Gly Ser His Phe Leu Tyr Ser Ile Leu Arg Val Thr Ala Asp Asp Trp
65                  70                  75                  80

Lys Lys Gly Asp Thr Phe Ser Cys Ser Val Met His Glu Ala Leu His
                85                  90                  95

Asn His Tyr Thr Gln Lys Ser Leu Asp Arg
            100                 105

<210> SEQ ID NO 9
<211> LENGTH: 106
<212> TYPE: PRT
<213> ORGANISM: Artificial sequence
<220> FEATURE:
<223> OTHER INFORMATION: Polypeptide sequence of GA(f3) SEED

<400> SEQUENCE: 9

Gly Gln Pro Arg Glu Pro Gln Val Tyr Thr Leu Pro Pro Ser Glu
1               5                   10                  15

Glu Leu Ala Leu Asn Glu Gln Val Thr Leu Thr Cys Leu Val Lys Gly
            20                  25                  30

Phe Tyr Pro Ser Asp Ile Ala Val Glu Trp Leu Gln Gly Ser Gln Glu
        35                  40                  45

Leu Pro Arg Glu Lys Tyr Leu Thr Trp Thr Pro Val Thr Asp Ser Asp
    50                  55                  60

Gly Ser Asp Phe Leu Tyr Ser Ile Leu Arg Val Thr Ala Asp Asp Trp
65                  70                  75                  80
```

```
Lys Lys Gly Asp Thr Phe Ser Cys Ser Val Met His Glu Ala Leu His
                85                  90                  95

Asn His Tyr Thr Gln Lys Ser Leu Asp Arg
            100                 105

<210> SEQ ID NO 10
<211> LENGTH: 106
<212> TYPE: PRT
<213> ORGANISM: Artificial sequence
<220> FEATURE:
<223> OTHER INFORMATION: Polypeptide sequence of AG(s0) SEED

<400> SEQUENCE: 10

Gly Gln Pro Phe Glu Pro Glu Val His Thr Leu Pro Pro Ser Arg Glu
1               5                   10                  15

Glu Met Thr Lys Asn Gln Val Ser Leu Thr Cys Leu Val Arg Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Ser Arg Leu Glu Pro Ser Gln Gly Thr
    50                  55                  60

Thr Thr Phe Ala Val Thr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu
            100                 105

<210> SEQ ID NO 11
<211> LENGTH: 106
<212> TYPE: PRT
<213> ORGANISM: Artificial sequence
<220> FEATURE:
<223> OTHER INFORMATION: Polypeptide sequence of GA(s0) SEED

<400> SEQUENCE: 11

Gly Gln Pro Arg Glu Pro Gln Val Tyr Thr Leu Pro Pro Ser Arg Glu
1               5                   10                  15

Glu Leu Ala Leu Asn Asn Gln Val Thr Leu Thr Cys Leu Val Lys Gly
            20                  25                  30

Phe Tyr Pro Ser Asp Ile Ala Val Glu Trp Glu Ser Asn Gly Gln Pro
        35                  40                  45

Glu Pro Arg Glu Lys Tyr Leu Thr Trp Ala Pro Val Leu Asp Ser Asp
    50                  55                  60

Gly Ser Phe Phe Leu Tyr Ser Ile Leu Arg Val Asp Ala Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu
            100                 105

<210> SEQ ID NO 12
<211> LENGTH: 9
<212> TYPE: PRT
<213> ORGANISM: Artificial sequence
<220> FEATURE:
<223> OTHER INFORMATION: Potential T-cell epitope in AG SEED
<400> SEQUENCE: 12

Phe Tyr Pro Lys Asp Ile Ala Val Glu
1               5
```

```
<210> SEQ ID NO 13
<211> LENGTH: 9
<212> TYPE: PRT
<213> ORGANISM: Artificial sequence
<220> FEATURE:
<223> OTHER INFORMATION: Potential T-cell epitope in AG SEED

<400> SEQUENCE: 13

Phe Ala Val Thr Ser Lys Leu Thr Val
1               5

<210> SEQ ID NO 14
<211> LENGTH: 9
<212> TYPE: PRT
<213> ORGANISM: Artificial sequence
<220> FEATURE:
<223> OTHER INFORMATION: Potential T-cell epitope in AG SEED

<400> SEQUENCE: 14

Val Thr Ser Lys Leu Thr Val Asp Lys
1               5

<210> SEQ ID NO 15
<211> LENGTH: 9
<212> TYPE: PRT
<213> ORGANISM: Artificial sequence
<220> FEATURE:
<223> OTHER INFORMATION: Potential T-cell epitope in AG SEED

<400> SEQUENCE: 15

Tyr Thr Gln Lys Thr Ile Ser Leu Ser
1               5

<210> SEQ ID NO 16
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 16

Leu Ala Leu Asn Glu Leu Val Thr Leu
1               5

<210> SEQ ID NO 17
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 17

Leu Asn Glu Leu Val Thr Leu Thr Cys
1               5

<210> SEQ ID NO 18
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 18

Leu Val Thr Leu Thr Cys Leu Val Lys
1               5
```

```
<210> SEQ ID NO 19
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 19

Tyr Leu Thr Trp Ala Pro Val Leu Asp
1               5

<210> SEQ ID NO 20
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 20

Leu Thr Trp Ala Pro Val Leu Asp Ser
1               5

<210> SEQ ID NO 21
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 21

Leu Asp Ser Asp Gly Ser Phe Phe Leu
1               5

<210> SEQ ID NO 22
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 22

Phe Phe Leu Tyr Ser Ile Leu Arg Val
1               5

<210> SEQ ID NO 23
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 23

Phe Leu Tyr Ser Ile Leu Arg Val Ala
1               5

<210> SEQ ID NO 24
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 24

Leu Tyr Ser Ile Leu Arg Val Ala Ala
1               5
```

```
<210> SEQ ID NO 25
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 25

Tyr Ser Ile Leu Arg Val Ala Ala Glu
1               5

<210> SEQ ID NO 26
<211> LENGTH: 9
<212> TYPE: PRT
<213> ORGANISM: Artificial sequence
<220> FEATURE:
<223> OTHER INFORMATION: Potential T-cell epitope in GA SEED

<400> SEQUENCE: 26

Ile Leu Arg Val Ala Ala Glu Asp Trp
1               5

<210> SEQ ID NO 27
<211> LENGTH: 914
<212> TYPE: DNA
<213> ORGANISM: Homo sapiens

<400> SEQUENCE: 27
gagcccaaat cttctgacaa aactcacaca tgcccaccgt gcccaggtaa gccagcccag      60
gcctcgccct ccagctcaag gcgggacagg tgccctagag tagcctgcat ccagggacag     120
gccccagccg ggtgctgaca cgtccacctc catctcttcc tcagcacctg aactcctggg     180
gggaccgtca gtcttcctct tccccccaaa acccaaggac accctcatga tctcccggac     240
ccctgaggtc acatgcgtgg tggtggacgt gagccacgaa gaccctgagg tcaagttcaa     300
ctggtacgtg gacggcgtgg aggtgcataa tgccaagaca aagccgcggg aggagcagta     360
caacagcacg taccgtgtgg tcagcgtcct caccgtcctg caccaggact ggctgaatgg     420
caaggagtac aagtgcaagg tctccaacaa agccctccca gcccccatcg agaaaaccat     480
ctccaaagcc aaaggtggga cccgtggggt gcgagggcca catggacaga ggccggctcg     540
gcccaccctc tgccctgaga gtgaccgctg taccaacctc tgtccctaca ggcagccccg     600 agaaccaca ggtgtacacc ctgccccat cacgggagga tgaccaag aaccaggtca       660 gcctgacctg cctggtcaaa ggcttctatc ccagcgacat cgccgtggag tgggagagca     720
atgggcagcc ggagaacaac tacaagacca cgcctcccgt gctggactcc gacggctcct     780
tcttcctcta tagcaagctc accgtggaca agagcaggtg gcagcagggg aacgtcttct     840
catgctccgt gatgcatgag gctctgcaca accactacac gcagaagagc ctctccctgt     900
ccccgggtaa atga                                                      914

<210> SEQ ID NO 28
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding AG(f0) SEED

<400> SEQUENCE: 28
gccggctcgg cccaccctct gccctgagag tgaccgctgt accaacctct gtccctacag      60
ggcagccctt ccggccagag gtccacctgc tgcccccatc acgggaggag atgaccaaga     120
```

```
accaggtcag cctgacctgc ctggcacgcg gcttctatcc caaggacatc gccgtggagt    180
gggagagcaa tgggcagccg gagaacaact acaagaccac gccttcccgg caggagccca    240
gccagggcac caccaccttc gctgtgacct cgaagctcac cgtggacaag agcagatggc    300
agcaggggaa cgtcttctca tgctccgtga tgcatgaggc tctgcacaac cactacacgc    360
agaagaccat ctccctgtcc ccggg                                          385
```

<210> SEQ ID NO 29
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding AG(s0) SEED

<400> SEQUENCE: 29

```
gccggctcgg cccacccctct gccctgagag tgaccgctgt accaacctct gtccctacag     60
ggcagccctt cgaaccagag gtccacaccc tgcccccatc acgggaggag atgaccaaga    120
accaggtcag cctgacctgc ctggtccgcg gcttctatcc cagcgacatc gccgtggagt    180
gggagagcaa tgggcagccg gagaacaact acaagaccac gccttcccgg ctggagccca    240
gccagggcac caccaccttc gctgtgacct cgaagctcac cgtggacaag agcagatggc    300
agcaggggaa cgtcttctca tgctccgtga tgcatgaggc tctgcacaac cactacacgc    360
agaagagcct ctccctgtcc ccggg                                          385
```

<210> SEQ ID NO 30
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding GA(f0) SEED

<400> SEQUENCE: 30

```
gccggctcgg cccacccctct gccctgagag tgaccgctgt accaacctct gtccctacag     60
ggcagccccg agaaccacag gtgtacaccc tgcccccacc gtcggaggag ctggccctga    120
acgagctggt gacgctgacc tgcctggtca aggcttcta tcccagcgac atcgccgtgg     180
agtggctgca ggggtcccag gagctgcccc gcgagaagta cctgacttgg cacccgtgc    240 tggactccga cggctccttc ttcctctata gtatactgcg cgtggcagcc gaggactgga    300 agaagggga caccttctca tgctccgtga tgcatgaggc tctgcacaac cactacacgc    360
agaagagcct cgaccgctcc ccggg                                          385
```

<210> SEQ ID NO 31
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding GA(s0) SEED

<400> SEQUENCE: 31

```
gccggctcgg cccacccctct gccctgagag tgaccgctgt accaacctct gtccctacag     60
ggcagccccg agaaccacag gtgtacaccc tgcccccacc gtcggaggag ctggccctga    120
acaaccaggt gacgctgacc tgcctggtca aggcttcta tcccagcgac atcgccgtgg     180
agtgggagag caatgggcag ccggagcccc gcgagaagta cctgacttgg cacccgtgc    240
```

```
tggactccga cggctccttc ttcctctatt cgatactgcg cgtggacgca agcaggtggc    300
agcaggggaa cgtcttctca tgctccgtga tgcatgaggc tctgcacaac cactacacgc    360
agaagagcct ctccctgtcc ccggg                                          385
```

<210> SEQ ID NO 32
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding GA(f1) SEED

<400> SEQUENCE: 32

```
gccggctcgg cccaccctct gccctgagag tgaccgctgt accaacctct gtccctacag     60
ggcagccccg agaaccacag gtgtacaccc tgccccacc gtcggaggag ctggccctga    120
acgagcaggt gacgctgacc tgcctggtca aaggcttcta tcccagcgac atcgccgtgg    180
agtggctgca gggtcccag gagctgcccc gcgagaagta cctgacttgg accccgtgg     240 tggactccga cggctccttc ttcctctata gtatactgcg cgtgacagcc gatgactgga    300
agaaggggga caccttctca tgctccgtga tgcatgaggc tctgcacaac cactacacgc    360
agaagagcct cgaccgctcc ccggg                                          385
```

<210> SEQ ID NO 33
<211> LENGTH: 368
<212> TYPE: PRT
<213> ORGANISM: Artificial sequence
<220> FEATURE:
<223> OTHER INFORMATION: Polypeptide sequence of a Fc(AG(f0) SEED)-IL2

<400> SEQUENCE: 33

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Phe Arg Pro Glu Val His Leu Leu Pro Pro Ser Arg Glu Glu Met Thr
    130                 135                 140

Lys Asn Gln Val Ser Leu Thr Cys Leu Ala Arg Gly Phe Tyr Pro Lys
145                 150                 155                 160

Asp Ile Ala Val Glu Trp Glu Ser Asn Gly Gln Pro Glu Asn Asn Tyr
                165                 170                 175

Lys Thr Thr Pro Ser Arg Gln Glu Pro Ser Gln Gly Thr Thr Thr Phe
            180                 185                 190

Ala Val Thr Ser Lys Leu Thr Val Asp Lys Ser Arg Trp Gln Gln Gly
        195                 200                 205
```

```
Asn Val Phe Ser Cys Ser Val Met His Glu Ala Leu His Asn His Tyr
    210                 215                 220
Thr Gln Lys Thr Ile Ser Leu Ser Pro Gly Lys Ala Pro Thr Ser Ser
225                 230                 235                 240
Ser Thr Lys Lys Thr Gln Leu Gln Leu Glu His Leu Leu Asp Leu
                245                 250                 255
Gln Met Ile Leu Asn Gly Ile Asn Asn Tyr Lys Asn Pro Lys Leu Thr
            260                 265                 270
Arg Met Leu Thr Phe Lys Phe Tyr Met Pro Lys Lys Ala Thr Glu Leu
            275                 280                 285
Lys His Leu Gln Cys Leu Glu Glu Glu Leu Lys Pro Leu Glu Glu Val
    290                 295                 300
Leu Asn Leu Ala Gln Ser Lys Asn Phe His Leu Arg Pro Arg Asp Leu
305                 310                 315                 320
Ile Ser Asn Ile Asn Val Ile Val Leu Glu Leu Lys Gly Ser Glu Thr
                325                 330                 335
Thr Phe Met Cys Glu Tyr Ala Asp Glu Thr Ala Thr Ile Val Glu Phe
            340                 345                 350
Leu Asn Arg Trp Ile Thr Phe Cys Gln Ser Ile Ile Ser Thr Leu Thr
            355                 360                 365

<210> SEQ ID NO 34
<211> LENGTH: 235
<212> TYPE: PRT
<213> ORGANISM: Artificial sequence
<220> FEATURE:
<223> OTHER INFORMATION: Polypeptide sequence of a Fc(GA(f0) SEED)

<400> SEQUENCE: 34

Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Glu Glu Leu Ala
130                 135                 140
Leu Asn Glu Leu Val Thr Leu Thr Cys Leu Val Lys Gly Phe Tyr Pro
145                 150                 155                 160
Ser Asp Ile Ala Val Glu Trp Leu Gln Gly Ser Gln Glu Leu Pro Arg
                165                 170                 175
Glu Lys Tyr Leu Thr Trp Ala Pro Val Leu Asp Ser Asp Gly Ser Phe
            180                 185                 190
Phe Leu Tyr Ser Ile Leu Arg Val Ala Ala Glu Asp Trp Lys Lys Gly
        195                 200                 205
```

```
Asp Thr Phe Ser Cys Ser Val Met His Glu Ala Leu His Asn His Tyr
    210                 215                 220
Thr Gln Lys Ser Leu Asp Arg Ser Pro Gly Lys
225                 230                 235

<210> SEQ ID NO 35
<211> LENGTH: 582
<212> TYPE: PRT
<213> ORGANISM: Artificial sequence
<220> FEATURE:
<223> OTHER INFORMATION: Polypeptide sequence of DI-KS(AG(f0) SEED)-IL2
      heavy chain

<400> SEQUENCE: 35

Gln Ile Gln Leu Val Gln Ser Gly Pro Glu Leu Lys Lys Pro Gly Ser
1               5                   10                  15
Ser Val Lys Ile Ser Cys Lys Ala Ser Gly Tyr Thr Phe Thr Asn Tyr
                20                  25                  30
Gly Met Asn Trp Val Arg Gln Ala Pro Gly Lys Gly Leu Lys Trp Met
            35                  40                  45
Gly Trp Ile Asn Thr Tyr Thr Gly Glu Pro Thr Tyr Ala Asp Asp Phe
        50                  55                  60
Lys Gly Arg Phe Thr Ile Thr Ala Glu Thr Ser Ser Thr Leu Tyr
65                  70                  75                  80
Leu Gln Leu Asn Asn Leu Arg Ser Glu Asp Thr Ala Thr Tyr Phe Cys
                85                  90                  95
Val Arg Phe Ile Ser Lys Gly Asp Tyr Trp Gly Gln Gly Thr Thr Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
```

```
Lys Ala Lys Gly Gln Pro Phe Arg Pro Glu Val His Leu Leu Pro Pro
                340                 345                 350

Ser Arg Glu Glu Met Thr Lys Asn Gln Val Ser Leu Thr Cys Leu Ala
            355                 360                 365

Arg Gly Phe Tyr Pro Lys Asp Ile Ala Val Glu Trp Glu Ser Asn Gly
        370                 375                 380

Gln Pro Glu Asn Asn Tyr Lys Thr Thr Pro Ser Arg Gln Glu Pro Ser
385                 390                 395                 400

Gln Gly Thr Thr Thr Phe Ala Val Thr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Thr Ile Ser Leu Ser Pro Gly
        435                 440                 445

Ala Ala Pro Thr Ser Ser Thr Lys Lys Thr Gln Leu Gln Leu Glu
    450                 455                 460

His Leu Leu Leu Asp Leu Gln Met Ile Leu Asn Gly Ile Asn Asn Tyr
465                 470                 475                 480

Lys Asn Pro Lys Leu Thr Arg Met Leu Thr Phe Lys Phe Tyr Met Pro
                485                 490                 495

Lys Lys Ala Thr Glu Leu Lys His Leu Gln Cys Leu Glu Glu Glu Leu
            500                 505                 510

Lys Pro Leu Glu Glu Val Leu Asn Leu Ala Gln Ser Lys Asn Phe His
        515                 520                 525

Leu Arg Pro Arg Asp Leu Ile Ser Asn Ile Asn Val Ile Val Leu Glu
530                 535                 540

Leu Lys Gly Ser Glu Thr Thr Phe Met Cys Glu Tyr Ala Asp Glu Thr
545                 550                 555                 560

Ala Thr Ile Val Glu Phe Leu Asn Arg Trp Ile Thr Phe Cys Gln Ser
                565                 570                 575

Ile Ile Ser Thr Leu Thr
            580

<210> SEQ ID NO 36
<211> LENGTH: 449
<212> TYPE: PRT
<213> ORGANISM: Artificial sequence
<220> FEATURE:
<223> OTHER INFORMATION: Polypeptide sequence of DI-KS(GA(f0) SEED)
      heavy chain

<400> SEQUENCE: 36

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Thr Ile Thr Ala Glu Thr Ser Thr Ser Thr Leu Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110
```

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Pro Ser Glu Glu Leu Ala Leu Asn Glu Leu Val Thr Leu Thr Cys Leu
        355                 360                 365

Val Lys Gly Phe Tyr Pro Ser Asp Ile Ala Val Glu Trp Leu Gln Gly
370                 375                 380

Ser Gln Glu Leu Pro Arg Glu Lys Tyr Leu Thr Trp Ala Pro Val Leu
385                 390                 395                 400

Asp Ser Asp Gly Ser Phe Phe Leu Tyr Ser Ile Leu Arg Val Ala Ala
                405                 410                 415

Glu Asp Trp Lys Lys Gly Asp Thr Phe Ser Cys Ser Val Met His Glu
            420                 425                 430

Ala Leu His Asn His Tyr Thr Gln Lys Ser Leu Asp Arg Ser Pro Gly
        435                 440                 445

Lys
```

<210> SEQ ID NO 37
<211> LENGTH: 213
<212> TYPE: PRT
<213> ORGANISM: Artificial sequence
<220> FEATURE:
<223> OTHER INFORMATION: Polypeptide sequence of DI-KS light chain

<400> SEQUENCE: 37

```
Gln Ile Val Leu Thr Gln Ser Pro Ala Ser Leu Ala Val Ser Pro Gly
1               5                   10                  15
Gln Arg Ala Thr Ile Thr Cys Ser Ala Ser Ser Ser Val Ser Tyr Ile
            20                  25                  30
Leu Trp Tyr Gln Gln Lys Pro Gly Gln Pro Pro Lys Pro Trp Ile Phe
        35                  40                  45
Asp Thr Ser Asn Leu Ala Ser Gly Phe Pro Ser Arg Phe Ser Gly Ser
    50                  55                  60
Gly Ser Gly Thr Ser Tyr Thr Leu Thr Ile Asn Ser Leu Glu Ala Glu
65                  70                  75                  80
Asp Ala Ala Thr Tyr Tyr Cys His Gln Arg Ser Gly Tyr Pro Tyr Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 38
<211> LENGTH: 20
<212> TYPE: DNA
<213> ORGANISM: Artificial sequence
<220> FEATURE:
<223> OTHER INFORMATION: linker fragment oligonucleotide

<400> SEQUENCE: 38
aattgccggg tcgacatacg                    20

<210> SEQ ID NO 39
<211> LENGTH: 20
<212> TYPE: DNA
<213> ORGANISM: Artificial sequence
<220> FEATURE:
<223> OTHER INFORMATION: linker fragment oligonucleotide

<400> SEQUENCE: 39
gatccgtatg tcgacccggc                    20

<210> SEQ ID NO 40
<211> LENGTH: 20
<212> TYPE: DNA
<213> ORGANISM: Artificial sequence
<220> FEATURE:
<223> OTHER INFORMATION: PCR primer

<400> SEQUENCE: 40
gccggctcgg cccaccctct                    20

```
<210> SEQ ID NO 41
<211> LENGTH: 22
<212> TYPE: DNA
<213> ORGANISM: Artificial sequence
<220> FEATURE:
<223> OTHER INFORMATION: PCR primer

<400> SEQUENCE: 41
cggcgatgtc gctgggatag aa                                              22

<210> SEQ ID NO 42
<211> LENGTH: 22
<212> TYPE: DNA
<213> ORGANISM: Artificial sequence
<220> FEATURE:
<223> OTHER INFORMATION: PCR primer

<400> SEQUENCE: 42
ttctatccca gcgacatcgc cg                                              22

<210> SEQ ID NO 43
<211> LENGTH: 31
<212> TYPE: DNA
<213> ORGANISM: Artificial sequence
<220> FEATURE:
<223> OTHER INFORMATION: PCR primer

<400> SEQUENCE: 43
cccggggaca gggagatgga cttctgcgtg t                                    31

<210> SEQ ID NO 44
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding AG(f1) SEED

<400> SEQUENCE: 44
gccggctcgg cccaccctct gccctgagag tgaccgctgt accaacctct gtccctacag     60
ggcagccctt ccggccagag gtccacctgc tgccccatc acgggaggag atgaccaaga     120
accaggtcag cctgacctgc ctggcacgcg gcttctatcc cagcgacatc gccgtggagt    180
gggagagcaa tggcagccg gagaacaact acaagaccac gccttcccgg caggagccca    240
gccagggcac caccaccttc gctgtgacct cgaagctcac cgtggacaag agcagatggc    300 agcagggaa cgtcttctca tgctccgtga tgcatgaggc tctgcacaac cactacacgc     360
agaagtccat ctccctgtcc ccggg                                          385

<210> SEQ ID NO 45
<211> LENGTH: 21
<212> TYPE: DNA
<213> ORGANISM: Artificial sequence
<220> FEATURE:
<223> OTHER INFORMATION: PCR primer

<400> SEQUENCE: 45
gctcttgtct gtggtgagct t                                               21

<210> SEQ ID NO 46
<211> LENGTH: 21
<212> TYPE: DNA
<213> ORGANISM: Artificial sequence
<220> FEATURE:
<223> OTHER INFORMATION: PCR primer
```

-continued

<400> SEQUENCE: 46
aagctcacca cagacaagag c                                              21

<210> SEQ ID NO 47
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding AG(f2) SEED

<400> SEQUENCE: 47
gccggctcgg cccaccctct gccctgagag tgaccgctgt accaacctct gtccctacag     60
ggcagccctt ccggccagag gtccacctgc tgccccatc acgggaggag atgaccaaga    120
accaggtcag cctgacctgc ctggcacgcg gcttctatcc cagcgacatc gccgtggagt    180
gggagagcaa tgggcagccg agaacaact acaagaccac gccttcccgg caggagccca    240
gccagggcac caccaccttc gctgtgacct cgaagctcac cacagacaag agcagatggc    300
agcaggggaa cgtcttctca tgctccgtga tgcatgaggc tctgcacaac cactacacgc    360
agaagtccat ctccctgtcc ccggg                                          385

<210> SEQ ID NO 48
<211> LENGTH: 50
<212> TYPE: DNA
<213> ORGANISM: Artificial sequence
<220> FEATURE:
<223> OTHER INFORMATION: PCR primer

<400> SEQUENCE: 48
tatagaggaa gtgggagccg tcggagtcgt ccacgggtgc ccaagtcagg              50

<210> SEQ ID NO 49
<211> LENGTH: 50
<212> TYPE: DNA
<213> ORGANISM: Artificial sequence
<220> FEATURE:
<223> OTHER INFORMATION: PCR primer

<400> SEQUENCE: 49
cctgacttgg gcacccgtgg acgactccga cggctcccac ttcctctata              50

<210> SEQ ID NO 50
<211> LENGTH: 21
<212> TYPE: DNA
<213> ORGANISM: Artificial sequence
<220> FEATURE:
<223> OTHER INFORMATION: PCR primer

<400> SEQUENCE: 50
cccggggagc ggtcgaggct c                                              21

<210> SEQ ID NO 51
<211> LENGTH: 103
<212> TYPE: PRT
<213> ORGANISM: Homo sapiens

<400> SEQUENCE: 51

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu
            100

<210> SEQ ID NO 52
<211> LENGTH: 109
<212> TYPE: PRT
<213> ORGANISM: Homo sapiens

<400> SEQUENCE: 52

Gly Asn Thr Phe Arg Pro Glu Val His Leu Leu Pro Pro Ser Arg Glu
 1               5                  10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
 50                  55                  60

Gln Gly Thr Thr Thr Phe Ala Val Thr Ser Ile Leu Arg Val Ala Ala
 65                  70                  75                  80

Glu Asp Trp Lys Lys Gly Asp Thr Phe Ser Cys Met Val Gly His Glu
                 85                  90                  95

Ala Leu Pro Leu Ala Phe Thr Gln Lys Thr Ile Asp Arg
            100                 105

<210> SEQ ID NO 53
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding GA(f2) SEED

<400> SEQUENCE: 53
gccggctcgg cccacccctct gccctgagag tgaccgctgt accaacctct gtccctacag      60 ggcagcccg  agaaccacag gtgtacaccc tgccccacc gtcggaggag ctggccctga      120
acgagcaggt gacgctgacc tgcctggtca aaggcttcta tcccagcgac atcgccgtgg      180
agtggctgca ggggtcccag gagctgcccc gcgagaagta cctgacttgg gcaccgtgg       240 acgactccga cggctcccac ttcctctata gtatactgcg cgtgacagcc gatgactgga      300
agaaggggga caccttctca tgctccgtga tgcatgaggc tctgcacaac cactacacgc      360
agaagagcct cgaccgctcc ccggg                                             385

<210> SEQ ID NO 54
<211> LENGTH: 385
<212> TYPE: DNA
<213> ORGANISM: Artificial sequence
<220> FEATURE:
<223> OTHER INFORMATION: DNA fragment Ngo MIV / Sma I, containing
      sequence encoding GA(f3) SEED
```

```
<400> SEQUENCE: 54
gccggctcgg cccaccctct gccctgagag tgaccgctgt accaacctct gtccctacag        60 ggcagcccccg agaaccacag gtgtacaccc tgcccccacc gtcggaggag ctggccctga     120
acgagcaggt gacgctgacc tgcctggtca aaggcttcta tcccagcgac atcgccgtgg     180
agtggctgca ggggtcccag gagctgcccc gcgagaagta cctgacttgg accccgtga     240 ccgactccga cggctccgac ttcctctata gtatactgcg cgtgacagcc gatgactgga     300
agaaggggga caccttctca tgctccgtga tgcatgaggc tctgcacaac cactacacgc     360
agaagagcct cgaccgctcc ccggg                                            385
```

US 8,871,912 B2

ENGINEERED HETERODIMERIC PROTEIN DOMAINS

CROSS-REFERENCE TO RELATED APPLICATIONS

This application claims priority to and the benefit of U.S. Provisional Patent Application No. 60/785,474, filed on Mar. 24, 2006, the entire contents of which are incorporated by reference herein.

FIELD OF THE INVENTION

The invention relates to engineered heterodimeric protein domains and methods of making the same.

BACKGROUND OF THE INVENTION

Nature provides a large number of homodimeric proteins and protein domains that fall into families of related proteins. Such proteins and domains often form homodimers with themselves but do not form heterodimers with other family members. On the other hand, heterodimeric or heteromultimeric proteins are often useful. They provide novel therapeutics and research tools. For example, bispecific antibodies (BsAbs) capable of binding to at least two different antigens have significant potential in a wide range of clinical applications as targeting agents for in vitro and in vivo immunodiagnosis and therapy, and for diagnostic immunoassays. In the diagnostic area, BsAbs have been very useful in probing the functional properties of cell surface molecules and in defining the ability of the different Fc receptors to mediate cytotoxicity (Fanger et al. (1992) *Crit. Rev. Immunol.* 12:101-124, the teachings of which are hereby incorporated by reference.) However, when BsAbs are generated simply by co-expression of multiple components that can interact without specificity, a large number of species are often generated, and it is often difficult to separate the desired species from the undesired species. Therefore, it is desirable to have techniques for efficiently making heteromultimers. It is particularly desirable to generate antibody subunits that form heterodimers preferentially over forming homodimers so that BsAbs can be directly recovered from recombinant cell culture.

Methods for making heterodimeric proteins have been reported. For example, Stahl and Yancopoulos described the use of fusion proteins including two different receptor subunits to form soluble heterodimeric receptors that could bind to a given cytokine in circulation, and thus block the activity of that cytokine (see U.S. Pat. No. 6,472,179). Carter et al. described a "protuberance-into-cavity" approach for generating a heterodimeric Fc moiety (see U.S. Pat. No. 5,807,706).

These existing methods allow constructions of individual heterodimers, but do not provide general techniques for construction of multimeric proteins involving multiple domain interactions. Therefore, there is a need for a general system for designing heterodimeric pairs that can specifically assemble in an environment containing multiple different potential assembly partners.

SUMMARY OF THE INVENTION

The present invention provides a novel approach for designing protein domains that preferentially heterodimerize or heteromultimerize. In particular, the invention uses a "Strand Exchange Engineered Domain" (SEED) strategy to engineer a protein-protein interaction interface that promotes heterodimerization or heteromultimerization. The invention also provides proteins containing domains engineered using the method of the present invention.

In one aspect, the present invention features a multidomain protein including at least first and second nonidentical engineered domains, each of which contains a protein-protein interaction interface containing amino acid sequence segments derived from two or more naturally-occurring homologous parent domains, thereby conferring on the first and second engineered domains assembly specificities distinct from assembly specificities of the parent domains, wherein the first and second engineered domains form heterodimers with one another preferentially over forming homodimers (e.g., the heterodimers constitute more than 55%, 65%, 75%, 80%, 85%, 90%, or 95% of the total amount of dimers). The first and second engineered domains are not antibody variable domains. In some embodiments, the multidomain protein of the invention includes a first subunit containing the first engineered domain and a second subunit containing the second engineered domain. As used herein, an "amino acid sequence segment" includes any sequence segment containing two or more amino acids (e.g., three or more, four or more, five or more, six or more, seven or more, eight or more nine or more, or ten or more).

In preferred embodiments, the multidomain protein includes nonidentical domains engineered from naturally-occurring homologous parent domains that are immunoglobulin superfamily domains, such as, for example, antibody CH3 domains. In particular, the engineered domains are derived from IgG and IgA CH3 domains.

In some embodiments, the multidomain protein of the invention includes engineered domains that are part of polypeptide chains that are connected by a disulfide bond.

In one embodiment, one of the engineered domains contained in the multidomain protein of the invention includes at least two non-adjacent sequence segments derived from the same parent domain. In another embodiment, each of the first and second engineered domains includes at least two, three, or four or more non-adjacent sequence segments derived from the same parent domain. In another embodiment, at least one of the engineered domains includes sequence segments from each parent domain that are at least two amino acids in length. In another embodiment, at least one of the engineered domains includes sequence segments from each parent domain that are at least three, four, five or six amino acids in length.

In some embodiments, the multidomain protein of the invention includes a first bio-active domain. The first bio-active domain may occupy a position N-terminal or C-terminal to the first engineered domain.

In further embodiments, the multidomain protein may further include a second bio-active domain in addition to the first bio-active domain. In one embodiment, the second bio-active domain is associated with the second engineered domain and may occupy a position N-terminal or C-terminal to the second engineered domain. In an alternate embodiment, the second bio-active domain is also associated with the first engineered domain and may occupy a position opposite the first bio-active domain. For example, the first and second bio-active domains may occupy positions N-terminal and C-terminal, respectively, to the first engineered domain.

The multidomain protein of the present invention can be used to generate bispecific antibodies. For example, the multidomain protein may include a first bio-active domain containing an antibody variable domain and a second bio-active domain containing a second antibody variable domain with distinct specificity.

In another aspect, the invention provides a multidomain protein, wherein the first bio-active region contains two or more antibody variable domains of a first specificity or of a first combination of specificities. The multidomain protein may also contain a second bio-active region including two or more antibody variable domains of a second specificity or second combination of specificities. For example, the multidomain protein may include one or more single-chain Fv moieties, a diabody (one VH-VL chain), a single-chain diabody [a VH(1)-VL(2)-VH(2)-VL(1)], or other single-chain Fv fused repeats (of the same or different specificities.

In another aspect, the invention provides a multidomain protein, wherein the first bio-active region comprises two or more antibody variable domains of a first specificity or of a first combination of specificities. The multidomain protein further comprises a second bio-active region comprising two or more antibody variable domains of a second specificity or second combination of specificities that are substantially distinct from the first combination of specificities.

The present invention further contemplates a method of colocalizing bio-active domains when administered to a biological system. The method includes the step of administering to the biological system the multimeric protein including first and second bio-active domains as described above in various embodiments. In one embodiment, the biological system is a mammal. In more preferred embodiment, the biological system is a human.

In another aspect, the present invention provides a multidomain protein including at least first and second nonidentical engineered domains that meet at an interface. The interface of the first engineered domain contains at least two amino acid sequence segments, each segment being derived from a different naturally-occurring homologous parent domain, thereby conferring an assembly specificity distinct from the assembly specificity of the parent domains, wherein the first and second engineered domains form heterodimers with one another preferentially over forming homodimers. In a preferred embodiment, the second engineered domain also contains at least two amino acid sequence segments, each segment being derived from a different naturally-occurring homologous parent domain, thereby conferring an assembly specificity distinct from the assembly specificity of the parent domains, wherein the first and second engineered domains form heterodimers with one another preferentially over forming homodimers.

In yet another aspect, the present invention provides a multidomain protein including at least first and second non-identical engineered domains that meet at an interface, wherein (1) the first and second engineered domains are derived from two or more naturally-occurring homologous parent domains, (2) the interface from the first engineered domain comprises at least one amino acid sequence segment interacting with an amino acid sequence segment on the interface of the second engineered domain derived from the same parent domain, and (3) the first and second engineered domains form heterodimers with one another preferentially over forming homodimers.

In another aspect, the present invention provides a multimeric protein including a domain with an amino acid sequence derived from two or more homologous parent domains and an interaction surface on said domain that mediates multimerization and that comprises amino acids derived from more than one of the parent domains; and wherein the specificity of multimerization is enhanced by the presence of amino acids from different parent domains. In some embodiments, the domain is part of a polypeptide chain with a disulfide bond that enhances assembly.

In further aspect, the present invention features an engineered immunoglobulin domain containing a protein-protein interaction interface including amino acids from two or more parent immunoglobulin domains such that the protein-protein interaction interface confers on the engineered immunoglobulin domain assembly specificities that are distinct from assembly specificities of the parent immunoglobulin domains, wherein the engineered immunoglobulin domain is not an antibody variable domain. In preferred embodiments, the engineered immunoglobulin domain of the invention assembles with a partner domain with enhanced specificity compared to the parent domains. In some embodiments, the partner domain is an engineered immunoglobulin domain of the invention.

In yet another aspect, the present invention provides an engineered immunoglobulin superfamily domain containing a protein-protein interaction interface including amino acids from two or more parent immunoglobulin superfamily domains such that the protein-protein interaction interface confers on the engineered immunoglobulin superfamily domain interaction properties that are distinct from interaction properties of the parent immunoglobulin superfamily domains.

The invention also provides a multidomain protein comprising an engineered domain with the following properties. Firstly, the engineered domain comprises a protein-protein interaction interface. Secondly, the engineered domain is homologous to a family of naturally occurring domains, preferably such that the amino acid sequence of the engineered domain can be aligned with amino acid sequences of naturally occurring domains, which can further be aligned with each other. Preferably, the alignment of the amino acid sequences of the naturally occurring domains corresponds to an alignment of the three-dimensional structures of the naturally occurring domains. Thirdly, the interaction interface of the engineered domain comprises amino acids from corresponding sequence positions from two or more naturally-occurring parental domains. Fourthly, the amino acids in the interface of the engineered domain, considered as a group, are not all found in the corresponding interface of any single member of the homologous naturally occurring domains. Fifthly, the interaction interface of the engineered domain confers assembly properties distinct from any of the parental domains. Preferably, the assembly properties of the engineered domain are distinctive because the interaction interface has amino acids from two or more different parents that make specific contacts with assembly partners, thus acquiring an assembly specificity that is a hybrid between the assembly specificities of the parent domains.

Furthermore, the present invention provides nucleic acid encoding a multidomain protein as described in various embodiments above. In particular, the present invention provides nucleic acid encoding a multidomain protein including at least one bio-active domain. The present invention also provides cells containing the nucleic acid of the invention.

In another aspect, the present invention provides a method of designing a multidomain protein with domains that preferentially heterodimerize. The method includes the following steps: (a) selecting a first polypeptide, a second polypeptide, a third polypeptide and a fourth polypeptide, wherein the first and third polypeptides dimerize with each other, but not with the second or fourth polypeptide, and wherein said second and fourth polypeptides dimerize with each other, (b) composing an amino acid sequence of a first domain from the first and the second polypeptides comprising at least one assembly element from the first polypeptide, and (c) composing an amino acid sequence of a second domain from the third and fourth polypeptides comprising at least one assembly element from the third polypeptide, such that the assembly elements from the first and third polypeptides assemble with each other, promoting heterodimerization of the first and second domains.

In some embodiments, the method of the invention composes an amino acid sequence of the first domain further including an assembly element from the second polypeptide and an amino acid sequence of the second domain further including an assembly element from the fourth polypeptide such that the assembly elements from the second and fourth polypeptides assemble with each other, promoting heterodimerization of the first and second domains.

In some embodiments, step (b) or step (c) of the above-described method includes comparing three-dimensional structures of two or more of the first, second, third or fourth polypeptides. In some embodiments, identical first and third polypeptides are selected. In other embodiments, identical first and third polypeptides are selected and identical second and fourth polypeptides are selected.

In some embodiments, step (b) or step (c) of the above-described method includes comparing aligned amino acid sequences of two or more of the first, second, third or fourth polypeptides. In some embodiments, identical first and third polypeptides are selected. In other embodiments, identical first and third polypeptides are selected and identical second and fourth polypeptides are selected.

Other features, objects, and advantages of the present invention are apparent in the detailed description that follows. It should be understood, however, that the detailed description, while indicating preferred embodiments of the present invention, is given by way of illustration only, not limitation. Various changes and modifications within the scope of the invention will become apparent to those skilled in the art from the detailed description.

BRIEF DESCRIPTION OF THE DRAWINGS

The Figures are provided for illustration, not limitation.

FIG. 2 depicts the structural alignment of human IgG1 CH3 (SEQ ID NO:51) and human IgA CH3 (SEQ ID NO:52) domains. Residue numbers are shown above and below the sequences. IgG1 is numbered according to Kabat EU numbering, while IgA is sequentially numbered as in the PDB structure 1OW0. Bold letters designate the backbone positions that were included in the alignment described in Table 2 in Example 1. Diamonds designate residues that contact or come close to the dimerization interface in IgG1 and IgA homodimers.

FIG. 3A depicts the sequence alignments and secondary structure of human IgA (SEQ ID NO:52), IgG1 (SEQ ID NO:51) and daughter "Surface" SEED sequences "AG SURF" (SEQ ID NO:10) and "GA SURF" (SEQ ID NO:11), while

FIG. 6A depicts the secondary structure of wild type CH3.

FIG. 6B depicts the secondary structure of the "GA SEED," and shows the strand exchange pattern. Gray ▓ represents IgG sequence; white □ represents IgA sequence; and black ■ shows the exchange points, with a broader black band indicating residues that are conserved in both IgA and IgG.

FIG. 6C depicts the secondary structure of the "AG SEED," which contains a pattern opposite to the pattern of the "GA SEED".

FIG. 7A depicts the "GA SEED," where the N-terminus begins as IgG sequence and ends as IgA after exchanging seven times. In this structure, the upper layer of β-strands are in the outside sheet, while the layer behind forms the interface with the other CH3 domain.

FIG. 7B depicts the "AG SEED," beginning with IgA sequence. Here, the front β-strands form the interface, while the β-strands behind are on the outside of the dimer.

FIG. 7C depicts the putative heterodimeric structure of the "GA SEED" and "AG SEED." Translating the structure shown in FIG. 7A over the structure shown in FIG. 7B brings the interface surfaces together. The black residues form an approximate plane that is oriented vertically and perpendicular to the page. All residues to the left are dark gray (IgG), while all residues to the right are white (IgA). Thus, with white opposite white and gray opposite gray, the whole of the interface is well formed, as a fusion of the IgA and IgG interfaces. The alternative homodimers, (AG/AG and GA/GA) would each have their IgA side juxtaposed to their IgG side (on both sides of the dividing plane), and so are disfavored.

In FIG. 8 and FIG. 9, polypeptide chains that include the GA SEED are colored black, while the polypeptide chains that include the AG SEED are colored white. Within such polypeptide chains, antibody V regions that are part of the GA SEED-containing polypeptide chain are black with thin white stripes, while antibody V regions that are part of the AG SEED-containing polypeptide chain are white with thin black stripes. Light chain constant regions are shown with a checkerboard pattern. Antibody hinge regions are shown as thin ovals connected by an "S—S" and a thick line to represent the disulfide bonds between the hinge regions. Polypeptide linkers are represented with dashed lines.

Figure 8:
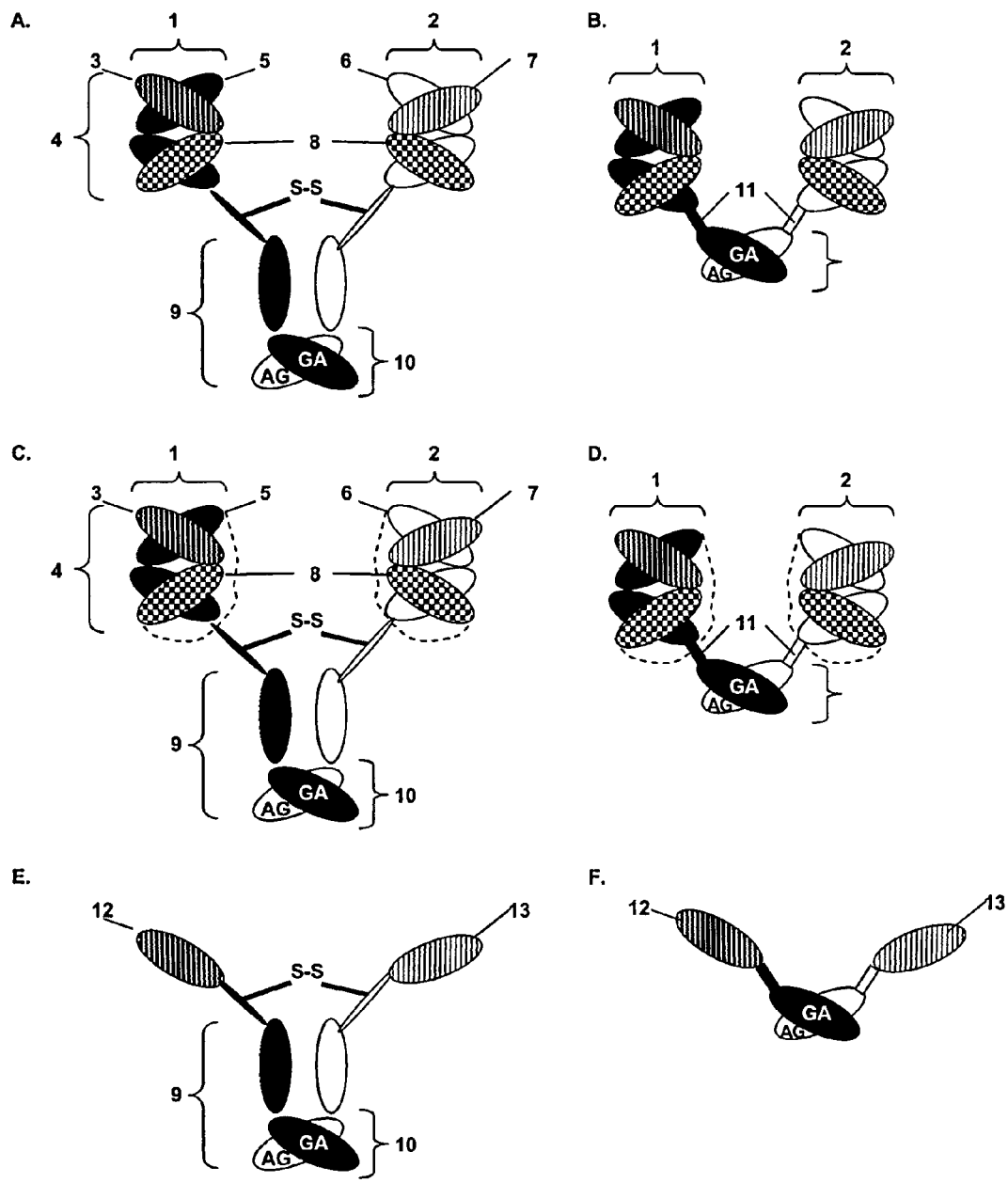
FIGS. 8-10 diagrammatically show a series of protein molecules that can be made using the SEED moieties described herein. For all of these figures, different moieties are indicated as follows.
Figure 9:
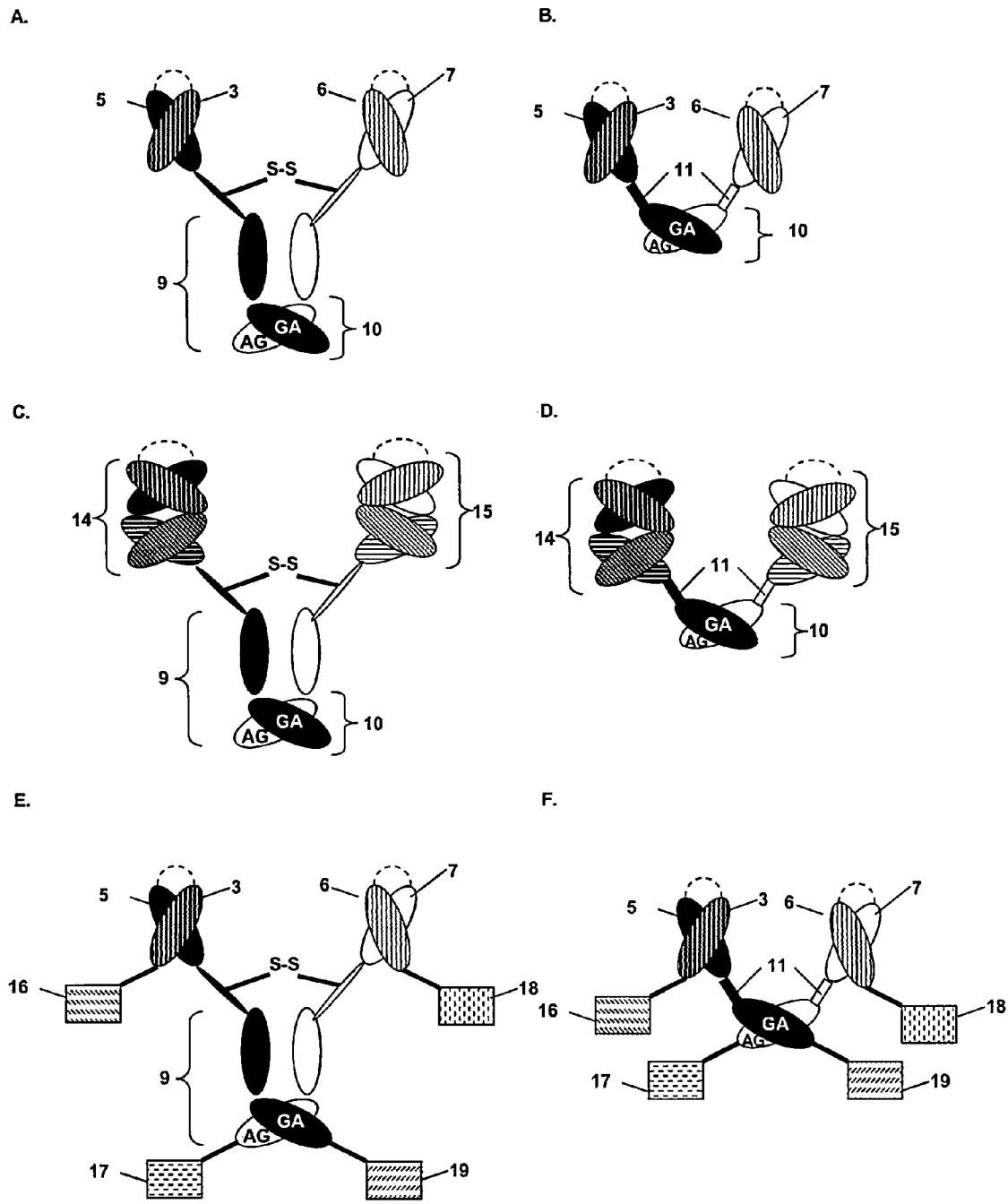
Figure 10:
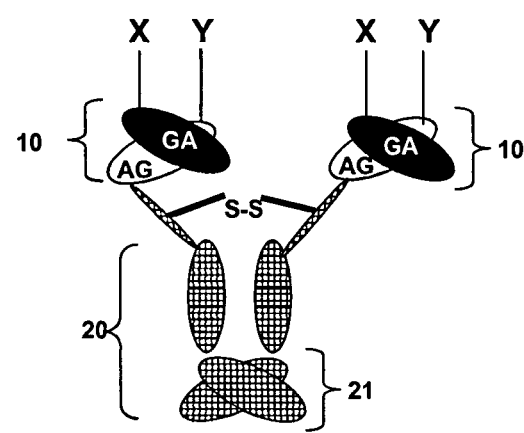

Portions of FIG. 8, FIG. 9, and FIG. 10 are numerically labeled as follows. In some cases, to simplify the figures, numerical labels are not shown, but the identity of the various domains and regions can be inferred from figures with corresponding domains and regions.

"1" indicates a GA-associated set of heavy and light chain V regions.

"2" indicates an AG-associated set of heavy and light chain V regions.

"3" indicates a GA-associated light chain V region.

"4" indicates an Fab region.

"5" indicates a GA-associated heavy chain V region.

"6" indicates an AG-associated heavy chain V region.

"7" indicates a AG-associated light chain V region.

"8" indicates a light chain constant region.

"9" indicates an Fc region comprising a SEED pair.

"10" indicates SEED pair.

"11" indicates an artificial linker.

"12" indicates a GA-associated single-domain or camelid V region.

"13" indicates an AG-associated single-domain or camelid V region.

"14" indicates a diabody or single chain fused diabody that is incorporated into the polypeptide chain comprising the GA SEED.

"15" indicates a diabody or single chain fused diabody that is incorporated into the polypeptide chain comprising the AG SEED.

"16", "17", "18", or "19" refers to any protein or peptide, such as a non-Ig domain. Such domains may include, for example, cytokines, hormones, toxins, enzymes, antigens, and extracellular domains of cell surface receptors.

"20" indicates a canonical homodimeric Fc region.

"21" indicates a canonical homodimeric pair of CH3 domains.

FIG. 8 illustrates types of antibody-type SEED configurations comprising moieties with essentially naturally occurring V regions, such as the Fab (FIG. 8A and FIG. 8B), single-chain Fab (FIG. 8C and FIG. 8D), and single-domain or camelid single-domain V regions (FIG. 8E and FIG. 8F). FIG. 8A, FIG. 8C, and FIG. 8E show molecules comprising an essentially intact Fc region, including CH2 domains, as well as a hinge. FIG. 8B, FIG. 8D, and FIG. 8F show molecules lacking a CH2 domain, in which the hinge is optionally replaced by a linker that optionally possesses or lacks cysteine residues capable of disulfide bonding.

FIG. 9 illustrates types of antibody-type SEED configurations comprising moieties with artificially configured V regions, such as single-chain Fvs (FIG. 9A and FIG. 9B), diabodies (FIG. 9C and FIG. 9D), and single-chain Fvs with additional moieties attached to the N- and/or C-termini of the two polypeptide chains (FIG. 9E and FIG. 9F). FIG. 9A, FIG. 9C, and FIG. 9E show molecules comprising an essentially intact Fc region, including CH2 domains, as well as a hinge. FIG. 9B, FIG. 9D, and FIG. 9F show molecules lacking a CH2 domain, in which the hinge is optionally replaced by a linker that optionally possesses or lacks cysteine residues capable of disulfide bonding.

FIG. 10 diagrammatically illustrates a molecule in which a GA/AG SEED pair essentially replaces the CH1-CL pairing in an antibody. Additional moieties, indicated by X and Y, may be placed at the N-termini of the GA and AG SEEDs. Moiety X and moiety Y can be, for example, a Fab, a single-chain Fab, a camelid single-domain V region, a single-chain Fv, a single-chain diabody such as that illustrated by "14" and "15" in FIG. 9C and FIG. 9D. Additional moieties may be fused to the C-termini of the CH3 domains indicated by "21".

Figure 11:
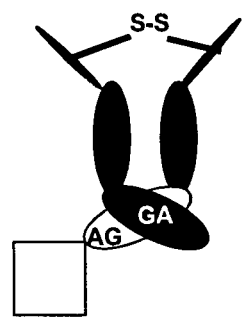
Figure 11:
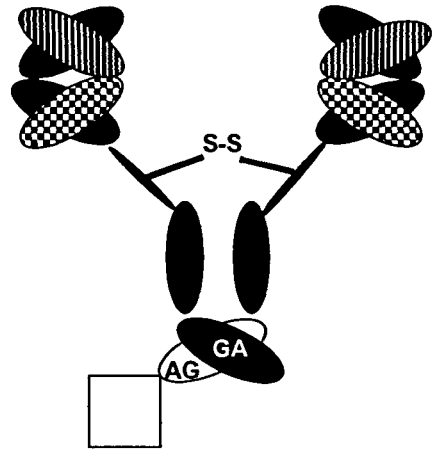

FIG. 11: FIG. 11A shows an Fc heterodimer produced as described in Example 5, in which an AG SEED moiety has an IL-2 moiety fused to its C-terminus. The CH2 and hinge moieties are identical in this case. FIG. 11B shows an antibody produced as described in Example 7, in which an AG SEED moiety has an IL-2 moiety fused to its C-terminus. Each antibody domain is represented by an oval, and the IL-2 moiety is represented by a white square. The CH2, CH1, hinge, VH, VL, and CL moieties are identical in this case. The hinge regions are attached by disulfide bonds represented by "S—S" in the figure. The light chain constant region is represented with a checkerboard pattern. The light chain V region is represented with a vertical-striped pattern. The VH, CH1, and CH2 regions are black.

Figure 12:
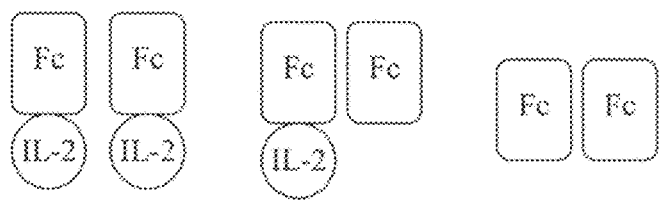
Figure 12:
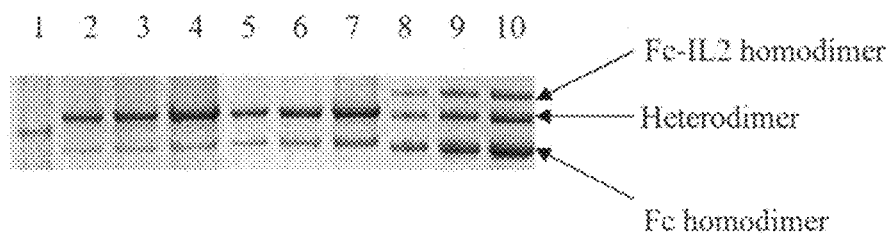
Figure 12:
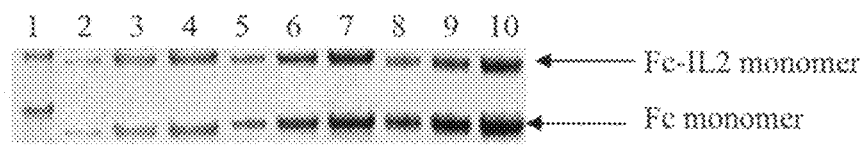

FIG. 12: FIGS. 12A-C depict the preferential assembly of AG/GA SEEDS into heterodimers as represented by the results of expression of Fc and Fc-IL2 in the same cell. FIG.

12A depicts the possible configurations of molecules resulting from coexpression of Fc and Fc-IL2, such that each dimeric species has a different molecular weight. FIG. 12B depicts a non-reducing SDS gel in which the following samples were loaded: lane 1—molecular weight standards; lane 2-4—about 1, 2, and 4 micrograms of total protein of the "full" Fc(GA SEED)/Fc(AG SEED)-IL2 expressed from NS/0 cells; lane 5-7—about 1, 2, and 4 micrograms of total protein of the "surface" Fc(GA SEED)/Fc(AG SEED)-IL2 expressed from NS/0 cells; lane 8-10—about 1, 2, and 4 micrograms of total protein of the parental IgG Fc/Fc-IL2 expressed from NS/0 cells. FIG. 12C is a reducing gel showing the ratio of expression of IgG-derived Fc and Fc-IL2.

FIGS. 12D-E depict Western blot analysis of non-reduced samples (panel D) and reduced samples (panel E) of the Fc/Fc-IL2 proteins of FIGS. 12B-C. Duplicate samples of "full" Fc(GA SEED)/Fc(AG SEED)-IL2 (lanes 1 and 4), "surface" Fc(GA SEED)/Fc(AG SEED)-IL2 (lanes 2 and 5), and parental Fc/Fc-IL2 (lanes 3 and 6) were loaded and the blot was probed using anti-human IgG Fc (lanes 1-3) and anti-human IL-2 (lanes 4-6) antibodies.

DETAILED DESCRIPTION OF THE INVENTION

The present invention provides methods for designing protein domains that preferentially heterodimerize or heteromultimerize. In particular, the invention uses a "Strand Exchange Engineered Domain" (SEED) strategy to engineer a protein-protein interaction interface that promotes heterodimerization or heteromultimerization. The invention also provides multidomain proteins containing domains engineered using this approach. Thus, the present invention represents a significant advance in protein engineering.

Various aspects of the invention are described in further detail in the following subsections. The use of subsections is not meant to limit the invention. Each subsection may apply to any aspect of the invention.

As used herein, a "multidomain protein" includes any protein containing two or more domains. The domains may be on single polypeptide; they may also be on different polypeptides. "Heteromultimerization" refers to nonidentical domains forming a multimeric complex mediated by domain interactions. A "heteromultimeric protein" is a protein molecule comprising at least a first subunit and a second subunit, each subunit contains a nonidentical domain. The heteromultimer can include a "heterodimer" formed by the first and second subunit or can form higher order structures (e.g., ternary) where subunit polypeptides in addition to the first and second subunit are present. Typically, each subunit contains a domain. Exemplary structures for the heteromultimer include heterodimers, heterotrimers, heterotetramers (e.g., a bispecific antibody) and further oligomeric structures.

As used herein, a "domain" includes any region of a polypeptide that is responsible for selectively assembling with an assembly partner of interest (e.g., another domain, ligand, receptor, substrate or inhibitor). Exemplary domains include an immunoglobulin superfamily constant domain such as a CH2 or CH3 domain, a receptor binding domain, a ligand binding domain, an enzymatic domain, or any polypeptide that has been engineered and/or selected to bind to a target. When two domains assemble with each other, they meet at a protein-protein interaction interface. As used herein, a "protein-protein interaction interface," an "interaction interface," or an "interface" includes those "contact" residues (amino acid or other non-amino acid residues such as carbohydrate groups, NADH, biotin, FAD or heme group) in the first domain that interact with one or more "contact" residues (amino acid or other non-amino acid groups) in the interface of the second domain. As used herein, a "contact" residue refers to any amino acid or non-amino acid residue from one domain that interacts with another amino acid or non-amino acid residue from a different domain by van der Waals forces, hydrogen bonds, water-mediated hydrogen bonds, salt bridges or other electrostatic forces, attractive interactions between aromatic side chains, the formation of disulfide bonds, or other forces known to one skilled in the art. Typically, the distance between alpha carbons of two interacting contact amino acid residues in the interaction interface is no greater than 12 Å. More typically, the distance between alpha carbons of two interacting contact amino acid residues in the interaction interface is no greater than 11 Å.

As used herein, a "parent domain" refers to any existing assembly domain as described above that can be used as a parent sequence for designing an engineered domain by the strand exchange strategy. Suitable parent domains are typically related or homologous and have particular assembly specificity. "Homologous" typically means two domains sharing at least 35%, 40%, 45%, 50%, 55%, 60%, 62%, 65%, 68%, 70%, 75%, 80%, 85%, 90%, 95% or 99% sequence identity. If parent domains are present in a common solution, they may tend to homodimerize rather than heterodimerize with one another. As used herein, "existing assembly domains" include wild-type or naturally-occurring sequences from organisms such as human, mouse, yeast, bacteria, to name but a few, as well as derivative sequences that have been modified from the wild-type sequences, such as, for example, sequences that have been stabilized; rendered less immunogenic; given altered, enhanced or diminished assembly specificity, altered enzymatic properties, altered solubility, or enhanced expression; truncated; or fused to another polypeptide. "Existing assembly domains" can also be partially- or fully-synthetic sequences that are synthesized based on molecular design, in vitro or in vivo selection methods (e.g., yeast two-hybrid system, phage display), or combinations thereof.

An "engineered domain" refers to a domain engineered from at least two nonidentical parent domains. An engineered domain is also referred to as a daughter domain. Typically, an engineered domain of the present invention contains amino acid sequence segments derived from two or more existing homologous parent domains. Preferably, the interface of an engineered domain includes amino acids derived from more than one parent domain. The presence of amino acids from different parent domains confers a assembly specificity distinct from the assembly specificities of the parent domains. For example, the presence of the amino acids from different parent domains promotes or enhances heterodimerization or heteromultimerization.

A Strand Exchange Engineered Domain (SEED) is an engineered domain that is engineered from at least two non-identical parent domains by the strand exchange engineering method described in detail below.

As used herein, a "polypeptide" refers generally to any polypeptide or protein having more than about ten amino acids. Preferably, mammalian polypeptides (polypeptides that were originally derived from a mammalian organism) are used for SEED engineering, more preferably those which are directly secreted into the medium. Examples of bacterial polypeptides include, e.g., alkaline phosphatase and β-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; α-1-antitrypsin; insulin A-chain;

insulin B-chain; proinsulin; follicle stimulating hormone; calcitonin; luteinizing hormone; glucagon; clotting factors such as factor VIIIC, factor IX, tissue factor, and von-Willebrands factor; anti-clotting factors such as Protein C; atrial natriuretic factor lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as AFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; regulatory proteins; immunoglobulins (antibodies); and fragments of any of the above-listed polypeptides.

As used herein, the "first polypeptide" or "first subunit" is any polypeptide which is to be associated with a second polypeptide through the interaction between the engineered domains. The "second polypeptide" or "second subunit" is any polypeptide which is to be associated with the first polypeptide through the interaction between the engineered domains. In addition to the engineered domains, the first and/or the second polypeptide may include one or more additional bio-active domains, such as, for example, an antibody variable domain, receptor binding domain, ligand binding domain or enzymatic domain) or other "binding domains" such as antibody constant domains (or parts thereof) including CH3 and CH2 domains. As an example, the first polypeptide may include at least one engineered domain of the invention, such as an engineered CH3 domain of an immunoglobulin and can form the interface of the first polypeptide. The first polypeptide may further include other antibody heavy chain binding domains (e.g., CH1, CH2, or CH4), and additional bio-active domains, such as receptor polypeptides (especially those which form dimers with another receptor polypeptide, e.g., interleukin-8 receptor and integrin heterodimers, e.g., LFA-1 or GPIIIb/IIIa), ligand polypeptides (e.g., cytokines, nerve growth factor, neurotrophin-3, and brain-derived neurotrophic factor—see Arakawa et al. (1994) *J. Biol. Chem.* 269(45):27833-27839 and Radziejewski et al. (1993) *Biochem.* 32(48):1350) and antibody variable domain polypeptides (e.g., diabodies and BsAbs).

As used herein, "assembly" refers to a protein-protein interaction that occurs during the production of a multisubunit protein. For example, during antibody production, the heavy and light chains are synthesized from ribosomes associated with the endoplasmic reticulum. The individual chains then fold, and then assemble into mature antibodies through proper association of heavy and light chains. For example, in the case of IgG antibodies, the assembly of the Fab portion is initially driven primarily by interactions between the CH1 and CL domains, and also by interactions between the VH and VL regions. In the case of the two heavy chains, the initial assembly reaction is the association of the two CH3 domains. These initial assembly reactions are usually, but not always, followed by disulfide bond formation between the assembled subunit polypeptides. As used herein, "assembly" is distinct from "binding"; assembly refers to the protein interaction events that occur during production of a mature protein, such as an antibody before it is secreted from a cell, while binding refers to protein interaction events that occur after secretion, such as the interaction of an antibody with an antigen or with an Fc receptor. In an operational sense, assembly of a therapeutic or diagnostic protein occurs during the preparation of the therapeutic protein up to and including the placement of a product in a vial, and binding of a therapeutic or diagnostic protein refers to events that occur after a therapeutic protein is administered to a patient or when a diagnostic protein is used in a diagnostic test.

By "binding" is meant the interaction of a protein with a target protein subsequent to the synthesis and assembly of the protein.

Strand Exchange Engineering

The invention uses the fact that natural protein domains mediating protein-protein interactions are often homologous or, in the case of homodimers, identical, and that such proteins and domains often only homodimerize with themselves but typically do not heterodimerize with other family members or do not heterodimerize with other family members with an affinity equal to or greater than their affinities for homodimerization. According to the invention, such proteins may be used to design heterodimeric or heteromultimeric proteins using strand exchange engineered methods described in detail below. Such engineered domains are also referred to as "Strand Exchange Engineered Domains" ("SEEDs"). Multidomain proteins containing such engineered domains are also referred to as strand exchange engineered proteins.

Strand exchange engineering typically begins with a structural model of a dimeric parent protein domain. Two parent domains that can each homodimerize or dimerize with its own assembly partner but not heterodimerize with each other are structurally aligned. The parent domains may dimerize in a face-to-face manner, i.e., the dimer partners may be related by a 180-degree rotational symmetry. The parent domains may also dimerize in a front-to-back manner.

Due to the geometry of rotational symmetry of homodimeric proteins, there is usually a line of amino acids in the interaction surface that interact in a homotypic manner. In other words, there are amino acids that interact with their counterparts in the other subunit. For example, in the CH3 domain of IgG1, these amino acids include L351, P352, T366, T394, P395, and Y407. This line of amino acids will generally be parallel to the axis of rotational symmetry of the dimer. In choosing parent domains, it is often useful to choose proteins that homodimerize such that the long axis of the dimerization interface is not strongly parallel to the axis of rotational symmetry. For example, SEEDs based on leucine-zipper family members are difficult to construct, because the dimerization interface is parallel to the axis of symmetry, and many of the amino acid interactions are homotypic. Accordingly, in some preferred embodiments, the engineered domains of the invention are not leucine-zipper domains. In contrast, the CH3 family domains are particular useful because a significant portion of the interaction surface lies outside the line of symmetry. It however will be recognized by those skilled in the art that the line of symmetry (i.e., a line of homotypically interacting amino acids) may be an oversimplification. For example, the side-chains of amino acids on the line of symmetry may point toward the hydrophobic core of the domain.

Figure 1A:
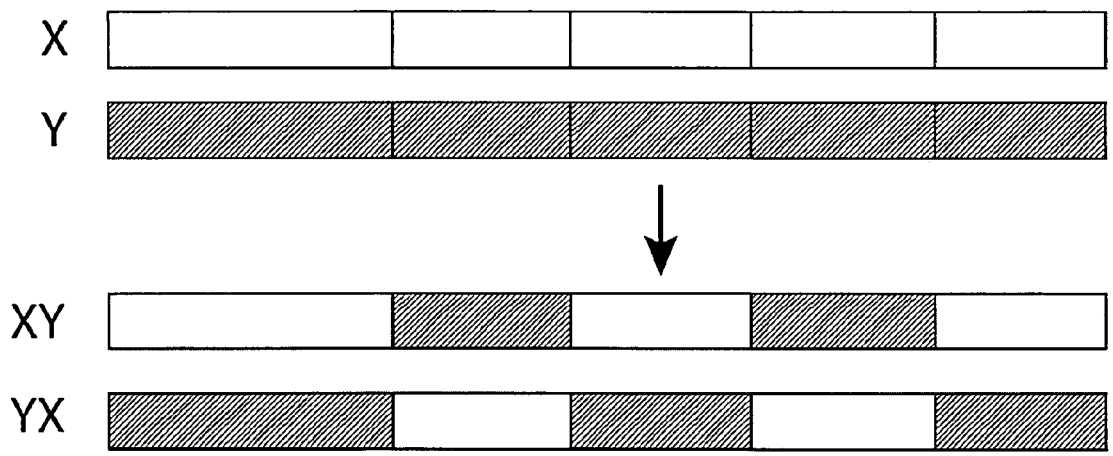
FIG. 1A schematically depicts an exemplary method of designing SEED constructs. Two related parent domains X and Y are aligned. The sequences of the two SEED subunits (XY and YX) are then generated by choosing for one SEED subunit alternating sequence segments from the two parental sequences, and choosing the complementary sequence segments to generate the other SEED subunit sequence. SEEDs engineered by this method are referred to as "Full" SEEDs.
Figure 1B:
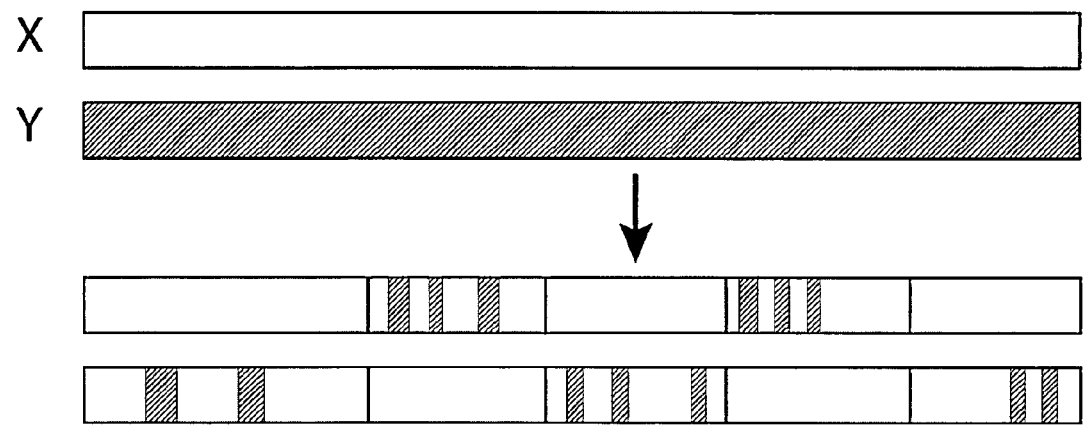
FIG. 1B schematically depicts a second exemplary method of designing SEED constructs, which is similar to FIG. 1A except that only amino acids forming the dimerization interface are chosen from one of the parental sequences. SEEDs engineered by this method are also referred to as "Surface" SEEDs.

A new dimerization interface is conceptually designed and divided into at least two regions which typically lie on either side of the homotypic interaction line (i.e., the line of symmetry). New domains are then designed by strand exchange wherein two daughter domain linear amino acid sequences are constructed from two aligned parent domain amino acid sequences by taking complementary segments from each parent sequence. As a result, in the regions of the dimerization interface, the two daughter domains (i.e., two SEEDs) have complementary amino acid segments from parent domains. This concept is illustrated in FIGS. 1A and 1B. As shown in FIG. 1A, two daughter SEED sequences, 1 and 2, are engineered from two parent sequences, A and B, in an entirely complementary manner. If Daughter 1 has an amino acid segment from Parent A at a given region of the interaction interface, Daughter 2 will have the corresponding amino acid segment from Parent B. The interaction interface is designed such that at least one amino acid sequence segment on Daughter 1 interacts with an amino acid sequence segment on daughter 2 that derived from the same parent domain. In FIG. 1B, the daughter SEED domains are derived primarily from one parent domain. However, the amino acids at the dimerization interface on either daughter SEED domain are derived from either one parent or another in a complementary manner.

It should be noted that FIG. 1A and FIG. 1B represent two extreme examples of the invention, and that SEEDs may be engineered by methods of the invention that have designs intermediate between FIG. 1A and FIG. 1B. For example, as described in the Examples in more detail, it is possible to construct a SEED based on parent domains from the immunoglobulin CH3 domain family. The daughter SEEDs may be derived primarily in a complementary manner from IgG and IgA, but the amino acids that interact with FcRn are derived from IgG to preserve the interaction with FcRn.

Thus, SEEDs are typically engineered by combining two or more homologous parent domains. The parent domains are polypeptides that differ from one another by at least four amino acids. In making a SEED, the sequences of the original polypeptides are aligned based on their homologies, theoretical structural models, crystal or solution structures, or any combinations thereof. There is at least one different amino acid at one or more aligned sequence positions, or a different number of amino acids in at least one pair of aligned original sequences. The parent sequences are then divided into at least two segments including at least one amino acid each. A SEED sequence may be composed by choosing, from among the original sequences, the one desired for each divided segment. A SEED will often differ from each individual parent sequence by at least two consecutive amino acids, and sometimes by three, four or more consecutive amino acids. In addition to selecting sequences from the original parent polypeptides, a SEED can contain any desired amino acids at any positions, such as positions outside the designed interface, in order to satisfy the other design needs.

There are positions on the sequence of the SEED where the parent sequence changes from one parent to a second parent. These positions are called exchange points or exchange positions. Exchange points or exchange positions can include one or more amino acids whose identity may be shared by both parents. Typically, exchange points are chosen from the amino acids on or near the line of symmetry, although other exchange points can also be chosen. Exchange points can also include amino acids not shared by the parents. In this case, the sequence abruptly switches from one parent to another. Furthermore, exchange points can include one or more novel amino acids not belonging to any of the parents. In this case, typically, different parent sequences appear on either side of the novel amino acids. If there are multiple exchange points in the sequence of a SEED, the total number of parent segments can be greater than two, up to a number one greater than the number of exchange points. These parent segments can be selected from distinct parent domains. Thus, the present invention contemplates SEEDs that are engineered from more than two parent domains.

For purposes of convenience, each SEED is typically named according to the order of its parent sequences, beginning with the N-terminus of the SEED. In the examples given below, an AG SEED has an IgA1 sequence segment on the N-terminal end, which then changes to an IgG1 sequence segment at the first exchange point. A GA SEED has an IgG1 sequence segment on the N-terminal end, which then changes to an IgA sequence at the first exchange point.

Thus, the interaction interface of the SEEDs of the invention includes amino acid sequence segments derived from two or more parent domains. As a result, the interface of the SEEDs has interaction properties distinct from interaction properties of the parent domains. In particular, the presence of amino acids from different parent domains confers an assembly specificity distinct from the assembly specificity of either of the parent domains. For example, the specificity of heterodimerization or heteromultimerization is enhanced by the presence of amino acids from different parent domains on the interface of a SEED. As a result, a pair of SEEDs form heterodimers with one another preferentially over forming homodimers. Thus, when a pair of SEEDs are expressed in an expression system, heterodimers of the SEEDs can specifically assemble such that the heterodimeric SEEDs can be directly recovered from the cell culture system without the need for elaborate separation steps to remove the homodimers.

CH3-Based SEEDs

Backbone homology and differences between the dimerization interfaces of the parent domains are important for creating SEEDs. Thus, according to one embodiment of the invention, the classes of immunoglobulin proteins are a useful source for parent domains. SEEDS can be created by using parental sequences from two different immunoglobulin classes. For example, SEEDs can be engineered from CH3 family domains by the method of the invention. CH3 family domains suitable for designing SEEDs include, but are not limited to, CH3 domains of IgG1, IgG2, IgG3, IgG4, IgA, and IgD, and the CH4 domains of IgE and IgM.

CH3 domains of human IgG1 and IgA form homodimers but do not form heterodimers with each other. Therefore, pairs of SEEDs (e.g., an AG SEED and a GA SEED) can be engineered from IgG1 and IgA CH3 domains such that they can heterodimerize with each other but their ability to homodimerize is minimal. According to one embodiment, the assembly interface on the CH3 domain is divided into two regions, which lie on either side of the line of homotypic interactions. Homotypic interactions for the IgA and IgG1 CH3 domains can be determined by observation and probing the crystal structure with a 1.4 Å sphere to determine whether or not the two side chains are close enough to exclude water. If the surfaces joined together across the interface, this implies that the side chains are closely interacting. For example, in the wild type CH3 domain of IgG1, the homotypically interacting amino acids include, but are not limited to, L351, P352, T366, T394, P395, and Y407. For the wild type CH3 domain of IgA1, the homotypically interacting amino acids include, but are not limited to, L352, P353, T368, W398, A399 and T414. In one exemplary SEED subunit, those amino acids with outwardly-pointing side-chains that lie to the left of the line of homotypic interaction are taken from the CH3 of IgG1, and those with outwardly-pointing side-chains to the right of the line of homotypic interaction are taken from the CH3 of IgA. In the other SEED subunit, those amino acids with outwardly-pointing side-chains that lie to the left of the line of homotypic interaction are taken from the CH3 of IgA, and those with outwardly-pointing side-chains to the right of the line of homotypic interaction are taken from the CH3 of IgG1. The choice of amino acids along the line of homotypic interaction is based on structural considerations and performed on a case-by-case basis, although it is likely that the amino acids from either parent domain can be selected for a particular region of a SEED.

For example, a CH3-based AG SEED may have a polypeptide sequence as shown in SEQ ID NO:1, wherein $X_1$, $X_2$, or $X_3$ may be any amino acids. In some embodiments, $X_1$ is K or S, $X_2$ is V or T, and $X_3$ is T or S. Preferably, $X_1$ is S, $X_2$ is V or T, and $X_3$ is S. A CH3-based GA SEED may have a polypeptide sequence as shown in SEQ ID NO:2, wherein $X_1$, $X_2$, $X_3$, $X_4$, $X_5$, or $X_6$ may be any amino acids. In some embodiments, $X_1$ is L or Q, $X_2$ is A or T, $X_3$ is L, V, D, or T, $X_4$ is F, A, D, E, G, H, K, N, P, Q, R, S, or T, $X_5$ is A or T, and $X_6$ is E or D. Preferably, $X_1$ is Q, $X_2$ is A or T, $X_3$ is L, V, D, or T, $X_4$ is F, A, D, E, G, H, K, N, P, Q, R, S, or T, $X_5$ is T, and $X_6$ is D. Exemplary SEED heterodimers may include one SEED subunit selected from AG(f0) SEED (SEQ ID NO:3), AG(f1) SEED (SEQ ID NO:4), or AG(f2) SEED (SEQ ID NO:5), and the other SEED subunit selected from GA(f0) SEED (SEQ ID NO:6), GA(f1) SEED (SEQ ID NO:7), GA(f2) SEED (SEQ ID NO:8), or GA(f3) SEED (SEQ ID NO:9). For example, a SEED heterodimer may include AG(f0) SEED (SEQ ID NO:3) and GA(f0) SEED (SEQ ID NO:6) subunits. In another example, a SEED heterodimer may include AG(f2) SEED (SEQ ID NO:5) and GA(f2) SEED (SEQ ID NO:8) subunits. In yet another embodiment, a SEED heterodimer may include AG(s0) SEED (SEQ ID NO:10) and GA(s0) SEED (SEQ ID NO:11) subunits.

Bio-Active Domains

The SEEDs according to this invention are particularly useful when coupled with a fusion partner. A fusion partner (X) can be fused to the N-terminus of the SEED (X-SEED), it can also be fused to the C-terminus of the SEED (SEED-X). In addition, a fusion partner can be fused to the N-terminus and the C-terminus of the SEED at the same time (X-SEED-X). Two different fusion partners can be fused to a SEED (X-SEED-Y).

Figure 1C:
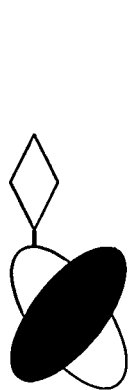
FIG. 1C depicts diagrammatically exemplary configurations of a SEED heterodimer, composed of a first daughter SEED (white oval) and a second daughter SEED (black oval), and a fusion partner, such as a bioactive domain (stalked white diamond). The SEED moiety and the fusion partner may be coupled by a linker segment (not depicted). In configurations with more than one fusion partner, the fusion partners may be identical to one another or distinct from one another, although in the diagrams they are shown generically as a stalked white diamond. The fusion partner may be N-terminal (A) or C-terminal (B) to the SEED moiety. There may be multiple concatenated fusion partners on one end of a SEED, as in (C), or the fusion partners may be located at opposite ends of a SEED (D). One fusion partner may be placed at N-terminal to a first daughter SEED and a second fusion partner may be placed N-terminal (F) or C-terminal (G) to a second daughter SEED. The SEED heterodimer may contain three (H) or four (I) fusion partners.
Figure 1C:
Figure 1C:
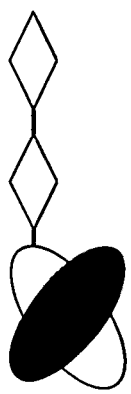
Figure 1C:
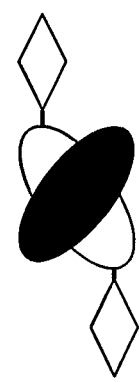
Figure 1C:
Figure 1C:
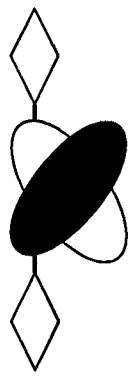
Figure 1C:
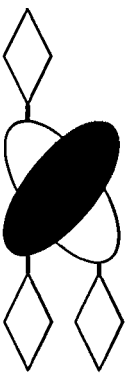
Figure 1C:
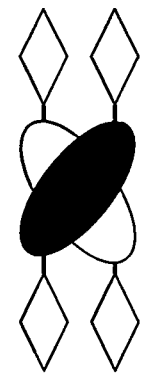

Given that two SEED sequences typically form heterodimers, it is possible that at least one, two, three, or four fusion partners can be contemplated in the SEED heterodimer. For example, according to one embodiment, the first daughter SEED has one fusion partner, and the second daughter SEED has no fusion partner, resulting in the following exemplary configurations: SEED-X heterodimerized to SEED; or X-SEED heterodimerized to SEED. In a further example, the first daughter SEED has two different fusion partners (X, Y), and the second daughter SEED has two different fusion partners (W, Z) differing from the fusion partners of the first daughter SEED. Possible exemplary configurations includes, but are not limited to: X-SEED-Y heterodimerized to W-SEED-Z; X-SEED-Y heterodimerized to Z-SEED-W; Y-SEED-X heterodimerized to W-SEED-Z; or Y-SEED-X heterodimerized to Z-SEED-W. According to the invention, a SEED can also have two or more fusion partners (X) fused sequentially to, for example, the N-terminus (X-X-SEED). Alternately, in another embodiment of the invention, the first daughter SEED has one fusion partner (X), and the second daughter SEED has one fusion partner (Y), resulting in the following exemplary configurations: X-SEED heterodimerized to Y-SEED; X-SEED heterodimerized to SEED-Y; or SEED-X heterodimerized to SEED-Y. In yet another embodiment of the invention, the first daughter SEED has one fusion partner (X), and the second daughter SEED has two fusion partners (Z, Y). Possible exemplary configurations include, but are not limited to: X-SEED heterodimerized to Y-SEED-Z; X-SEED heterodimerized to Z-SEED-Y; SEED-X heterodimerized to Z-SEED-Y; or SEED-X heterodimerized to Y-SEED-Z. Exemplary configurations are illustrated in FIG. 1C.

In particular, a fusion partner can be one or more bio-active domains including any biologically active protein or a biologically active portion thereof. For example, a bio-active domain can include an antibody constant or variable region, including, but not limited to, a VL domain, a VH domain, an Fv, a single-chain Fv, a diabody, an Fab fragment, a single-chain Fab, or an $F(ab')_2$.

According to the invention, the fusion partners can be coupled to the SEED moieties directly or indirectly. For example, a fusion partner may be linked to a SEED moiety by a peptide linker, such as described in U.S. Pat. No. 5,258,498 and U.S. Pat. No. 5,482,858 to Huston et al., or U.S. Pat. No. 5,856,456 and U.S. Pat. No. 5,990,275 to Whitlow et al., the teaching of which are hereby incorporated by reference. Typically, a suitable peptide linker may contain glycine and serine residues. Typically, a suitable peptide linker may also have different properties. For example, in some embodiments, a linker may further include a protease cleavage site, such as a matrix metalloproteinase recognition site.

Thus, the present invention provides a novel method to produce multispecific antibodies based on SEED technology. A multispecific antibody is a molecule having binding specificities for at least two different antigens. While such molecules typically will only bind two antigens (i.e. BsAbs), antibodies with additional specificities such as trispecific or tetraspecific antibodies are encompassed by this expression when used herein. Examples of BsAbs include those that bind to different antigens on the same cell surface, or those that bind to a cell surface antigen and a non-cell surface antigen. A non-cell surface antigen includes, but is not limited to, an extracellular or intracellular antigen, a soluble or insoluble antigen. The multispecific antibodies may bind to different antigens simultaneously, although simultaneous binding is not required for the function of the multispecific antibodies. In some applications, the antigens are preferentially functionally related, such as EGFR and HER2. Particularly useful types of multispecific antibodies include, but are not limited to, anti-EGFR/anti-HER2; anti-EGFR/anti-HER2/anti-HER3; anti-EGFR/anti-HER3; anti-EGFR/anti-HER2/anti-IGF1R; anti-EGFR/anti-HER2/anti-HER3/anti-IGF1R; anti-EGFR/anti-HER3/anti-IGF1R; anti-EGFR/anti-IGF1R; and anti-HER2/anti-IGF1R. Other combinations of specificities involving the EGFR, HER family and IGF1R are within the scope of the present invention.

Further examples of BsAbs include those with one arm directed against a tumor cell antigen and the other arm directed against a cytotoxic trigger molecule such as anti-FcγRI/anti-CD15, anti-185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti- CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g., FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37.

According to the invention, other bio-active domains include hormones, cytokines, chemokines, secreted enzymes, ligands, extracellular portions of trans-membrane receptors, or receptors. Hormones include, but are not limited to, growth hormones, or glucagon-like peptide (GLP-1). Cytokines include, but are not limited to, interleukin-2 (IL-2), IL-4, IL-5, IL-6, IL-7, IL-10, IL-12, IL-13, IL-14, IL-15, IL-16, IL-18, IL-21, IL-23, IL-31; hematopoeitic factors such as granulocyte-macrophage colony stimulating factor (GM-CSF), G-SCF and erythropoietin; tumor necrosis factors such as TNF-α; lymphokines such as lymphotoxin; regulators of metabolic processes such as leptin; and interferons (IFN) such as IFN-α, IFN-β, and IFN-γ.

Thus, the engineered heteromeric proteins of the present invention permit the colocalization of different bio-active domains in a biological system. This can be accomplished, for example, in the context of a multimeric protein incorporating two different antibody variable domains, where one antibody variable domain is fused to one engineered domain and a second antibody variable domain is fused to a second engineered domain that preferentially assembles with the first engineered domain. Administration of such an engineered protein causes two distinct activities—in this case, binding activities—to be present in the same molecule in the biological system, colocalizing the activities within the biological system. Whether the activities involve binding to other molecules (as an antibody variable domain/antigen interaction, a ligand/receptor interaction, etc.), enzymatic activities, or a combination thereof, the present invention provides a system to require that the activities be present at the same place permitting, for example, the targeting of a therapeutic activity to a particular cell type or location; the crosslinking of different receptors or cells; the colocalization of an antigen and adjuvant; etc. This can be accomplished by direct administration of an engineered heteromeric protein to a biological system or by expression of nucleic acid encoding the subunits within the biological system. Nucleic acid expression permits the engineering of additional levels of control in the system. For example, the expression of each subunit can be differentially regulated, such that the complete heteromeric protein and the resulting colocalization of activities occurs only upon the occurrence of all conditions required for expression of each subunit.

Engineered Domains with Reduced Immunogenicity

In another embodiment of the invention, the SEED sequences can be modified to reduce their potential immunogenicity. Because SEED polypeptides are hybrids between two different naturally occurring human sequences, they include sequence segments at their junctions that are not found in natural human proteins. In an organism, these sequence segments may be processed into non-self T-cell epitopes.

Methods to analyze peptide sequences for their potential to create T-cell epitopes are well known in the art. For example, ProPred (Singh and Raghava (2001) *Bioinformatics* 17:1236-1237) is a publicly available web-based toll that can be used for the prediction of peptides that bind HLA-DR alleles. ProPred is based on a matrix prediction algorithm described by Sturniolo for a set of 50 HLA-DR alleles (Sturniolo et al., (1999) *Nature Biotechnol.* 17:555-561). Using such an algorithm, various peptide sequences were discovered within AG SEED and GA SEED polypeptide sequences which are predicted to bind to multiple MHC class II alleles with significant binding strength and are therefore potentially immunogenic.

For example, in one embodiment, the AG SEED and GA SEED sequences are modified to remove one or more T-cell epitopes present in the SEED sequence. This modification may include substitution, deletion, or modification of one or more amino acid residues in order to remove the T-cell epitope. Table 1 presents a list of peptide sequences that are potential T-cell epitopes in the AG SEED and GA SEED, and possible amino acid substitutions that are predicted to reduce or remove the T-cell epitope.

TABLE 1

AG(f0) SEED

| Pos | Peptide | | Amino Acid Substitution |
|---|---|---|---|
| 32 | FYPKDIAVE | (SEQ ID NO: 12) | K35S |
| 67 | FAVTSKLTV | (SEQ ID NO: 13) | V75T |
| 69 | VTSKLTVDK | (SEQ ID NO: 14) | |
| 99 | YTQKTISLS | (SEQ ID NO: 15) | T103S |
| 18 | LALNELVTL | (SEQ ID NO: 16) | L23Q |
| 20 | LNELVTLTC | (SEQ ID NO: 17) | |
| 23 | LVTLTCLVK | (SEQ ID NO: 18) | |
| 54 | YLTWAPVLD | (SEQ ID NO: 19) | A58T |
| 55 | LTWAPVLDS | (SEQ ID NO: 20) | L61V, D, T |
| 61 | LDSDGSFFL | (SEQ ID NO: 21) | L61V, D, T |
| 67 | FFLYSILRV | (SEQ ID NO: 22) | F67A, D, E, G, H, K, N, P, Q, R, S, T |
| 68 | FLYSILRVA | (SEQ ID NO: 23) | A76T |

TABLE 1-continued

AG(f0) SEED

| Pos | Peptide | Amino Acid Substitution |
|---|---|---|
| 69 | LYSILRVAA (SEQ ID NO: 24) | E78D |
| 70 | YSILRVAAE (SEQ ID NO: 25) | |
| 72 | ILRVAAEDW (SEQ ID NO: 26) | |

Table 1 shows peptides in AG(f0) SEED or GA(f0) SEED which are predicted to bind to HLA-DR alleles and are potential T-cell epitopes, and amino acid substitutions at specific residues (indicated in bold) within the peptides that are predicted to reduce the binding to HLA-DR alleles. "Pos" indicates the position of the peptide within the sequence. The numbering of the amino acids is sequential and relative to the first amino acid of the SEED molecule.

The original "full" AG SEED (AG(f0) SEED (SEQ ID NO:3)) and GA SEED (GA(f0) SEED (SEQ ID NO:6)) polypeptides, and some exemplary variant polypeptides, including AG(f1) SEED (SEQ ID NO:4), AG(f2) SEED (SEQ ID NO:5), GA(f1) SEED (SEQ ID NO:7), GA(f2) SEED (SEQ ID NO:8), and GA(f3) SEED (SEQ ID NO:9) are shown in the following alignments.

```
Alignment of AG SEEDs (dot indicates residue identity)
 1 GQPFRPEVHLLPPSREEMTKNQVSLTCLARGFYPKDIAVEWESNGQPENNYKTTPSRQEP  AG(f0) SEED 1 ...............................S...........................  AG(f1) SEED 1 ...............................S...........................  AG(f2) SEED 61 SQGTTTFAVTSKLTVDKSRWQQGNVFSCSVMHEALHNHYTQKTISL                AG(f0) SEED 61 ..........................................S...              AG(f1) SEED 61 ..............T...........................S...              AG(f2) SEED Alignment of GA SEEDs (dot indicates residue identity)
 1 GQPREPQVYTLPPPSEELALNELVTLTCLVKGFYPSDIAVEWLQGSQELPREKYLTWAPV  GA(f0) SEED 1 .......................Q................................T..  GA(f1) SEED 1 .......................Q....................................  GA(f2) SEED 1 .......................Q................................T..  GA(f3) SEED 61 LDSDGSFFLYSILRVAAEDWKKGDTFSCSVMHEALHNHYTQKSLDR                GA(f0) SEED 61 V.............T.D.............                               GA(f1) SEED 61 D.....H.......T.D.............                               GA(f2) SEED 61 T.....D.......T.D.............                               GA(f3) SEED
```

Further exemplary embodiments according to the invention are detailed in the examples that follow.

EXAMPLES

Example 1

Identifying Homologous Structures to Become Parents of a Seed

In this set of examples, the goal is to produce two distinct CH3-homolog SEEDs that will form dimers that favor the formation of a heterodimer over formation of the two possible homodimers, thus resulting in a predominance of CH3-homolog heterodimers. The first task is to identify two or more CH3 domains that may produce this result when they are used as parents of a pair of SEEDs. The CH3 homodimer forms a dimerization interface between β-sheets. It is important to find two CH3 domains that have significant differences in this interface, in order to make an effective pair of SEEDs that will preferentially heterodimerize.

CH3 domains from IgG are structurally highly conserved across the animal kingdom, containing a classic immunoglobulin domain β-sandwich fold. While there are significant differences between species in the identities of the amino acids found on the outer surface, the dimerization interface surface that is buried upon dimerization is mostly conserved.

Each different class of immunoglobulin has its own Fc, and in particular has its own equivalent of the IgG CH3 sequence and structure. Examination of the CH3 domain in the crystal structure of the Fc portion of a human IgA1 (PDB number 1OW0, resolution 3.1 Å) revealed that the overall fold was homologous to human IgG CH3. The backbone RMSD (root mean square deviation) of the alignment of single CH3 domains from the IgA Fc 1OW0 and from the IgG Fc 1L6X, excluding turns where alignment had different lengths, was about 0.99 Å (See table 2). However, the CH3 homodimer interface of IgA1 is significantly different than that of IgG1. Thus, two SEEDs made from the CH3 of human IgA1 and the CH3 of human IgG1 each contain some portion of the interface from IgA1, and some from IgG1, and are designed to not dimerize with themselves, nor with either parent CH3, but to dimerize preferentially with the other complementary SEED.

TABLE 2

Structural alignment of CH3 domains from IgG and IgA*

| Human IgG | Human IgA |
|---|---|
| Q342-M358 | N343-L359 |
| N361-P387 | E363-E389 |

TABLE 2-continued

Structural alignment of CH3 domains from IgG and IgA*

| Human IgG | Human IgA |
|---|---|
| N390-S400 | K394-P404 |
| G402-L443 | T409-R450 |

*Portions of IgG and IgA sequences were used to overlay structures and determine backbone RMSD. The program InsightII ® (Accelrys, San Diego, CA) superimposed the backbone atoms of the residues included in the structurally homologous sequences listed above. The RMSD between the two backbones (within the ranges in the table) was 0.99 Å.

For example, the CH3 domain from human IgA1 and the CH3 domain from human IgG1 were used as parental polypeptides. For structural alignment and modeling, IgG1 PDB entries 1DN2 (resolution 2.7 Å) and 1L6X (CH3 sequence highly homologous to 1DN2, with two minor differences, resolution 1.65 Å), and IgA1 PDB entry 1OW0 (resolution 3.1 Å) were used. FIG. 2 shows the structural alignment of the two sequences. The CH3 domain of IgG1 is numbered according to Kabat EU Index (Kabat et al., (1991) *Sequences of Proteins of Immunological Interest 5$^{th}$* Edition, NIH Publication 91-3242), while the CH3 domain of IgA is sequentially numbered as in the PDB structure 1OW0. Bold letters designate the backbone positions that were included in the alignment described in Table 2, which were further used to design junctional crossover points in designing SEEDs.

Example 2

Choice of Exchange Points

Figure 4:
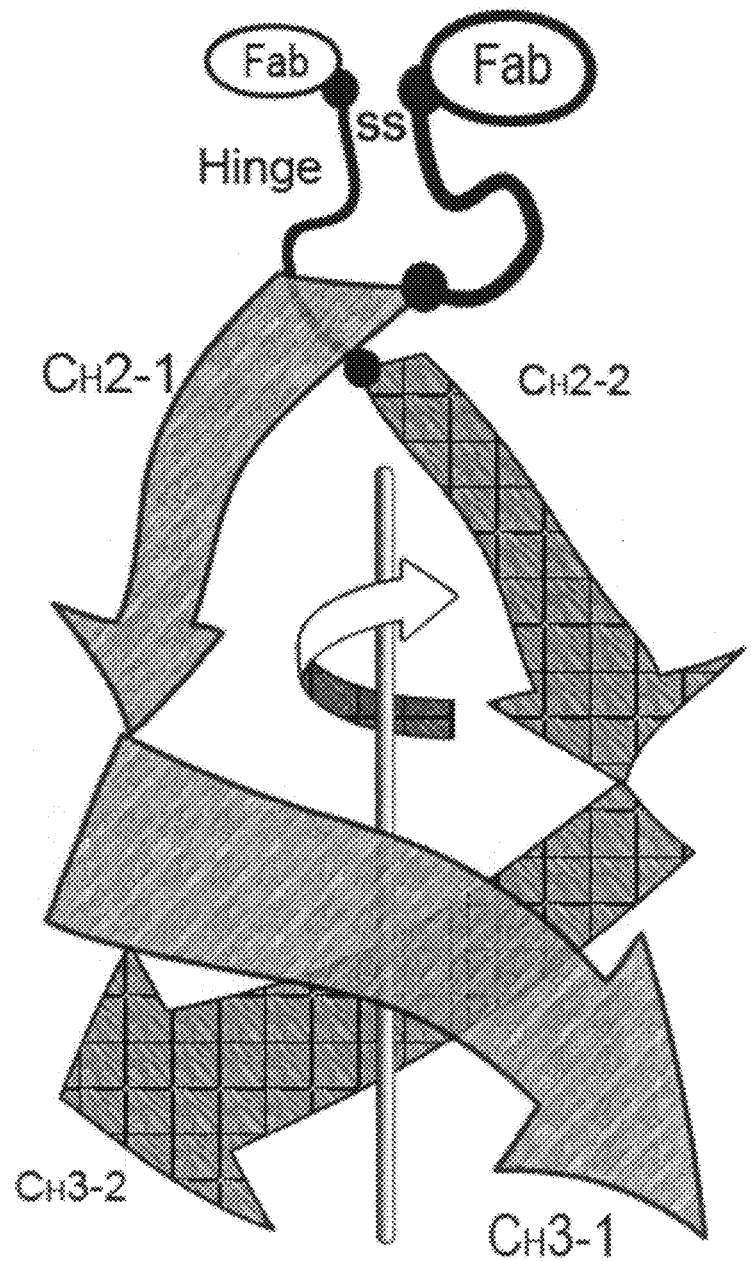
FIG. 4 is a representation of an IgG antibody molecule illustrating the symmetry of the CH3 homodimer. The vertical bar designates the axis of 2-fold rotational symmetry.
Figure 5:
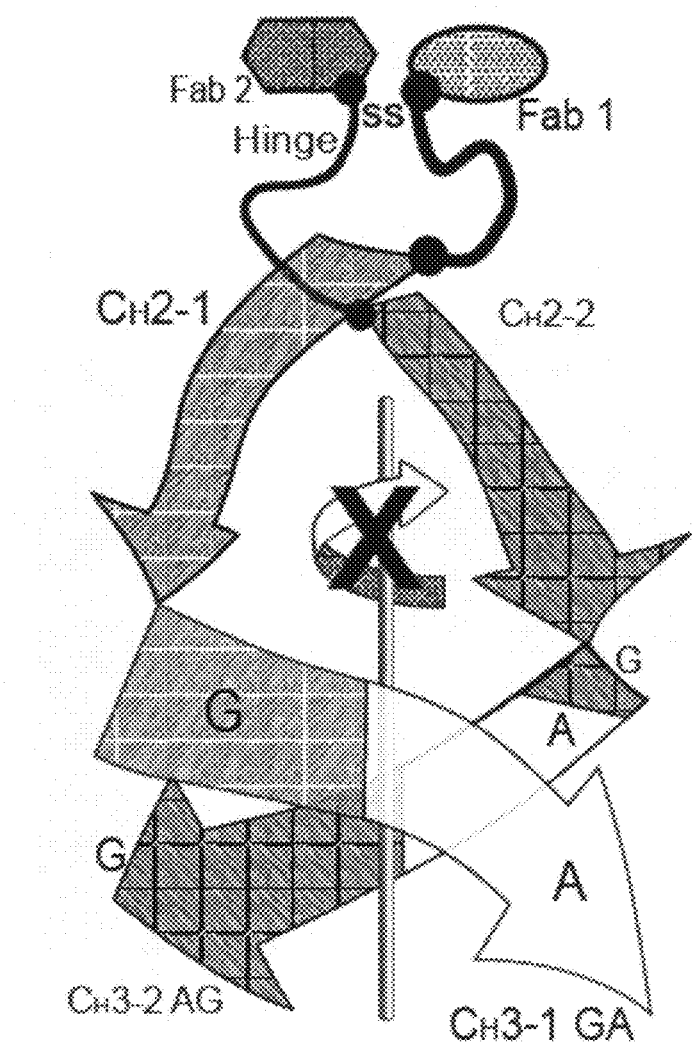
FIG. 5 is a representation of a bispecific, antibody-like molecule having two different Fab domains, paired by the heterodimeric SEED analogue of the CH3 domain. The hashed, gray portion represents the IgG-derived portion, while the white □ represents the IgA-derived portion. The symmetry of the CH3 complex is broken in the AG/GA heterodimer, as represented by the "X" on the vertical bar designating the axis of two-fold rotational symmetry.
Figure 6:
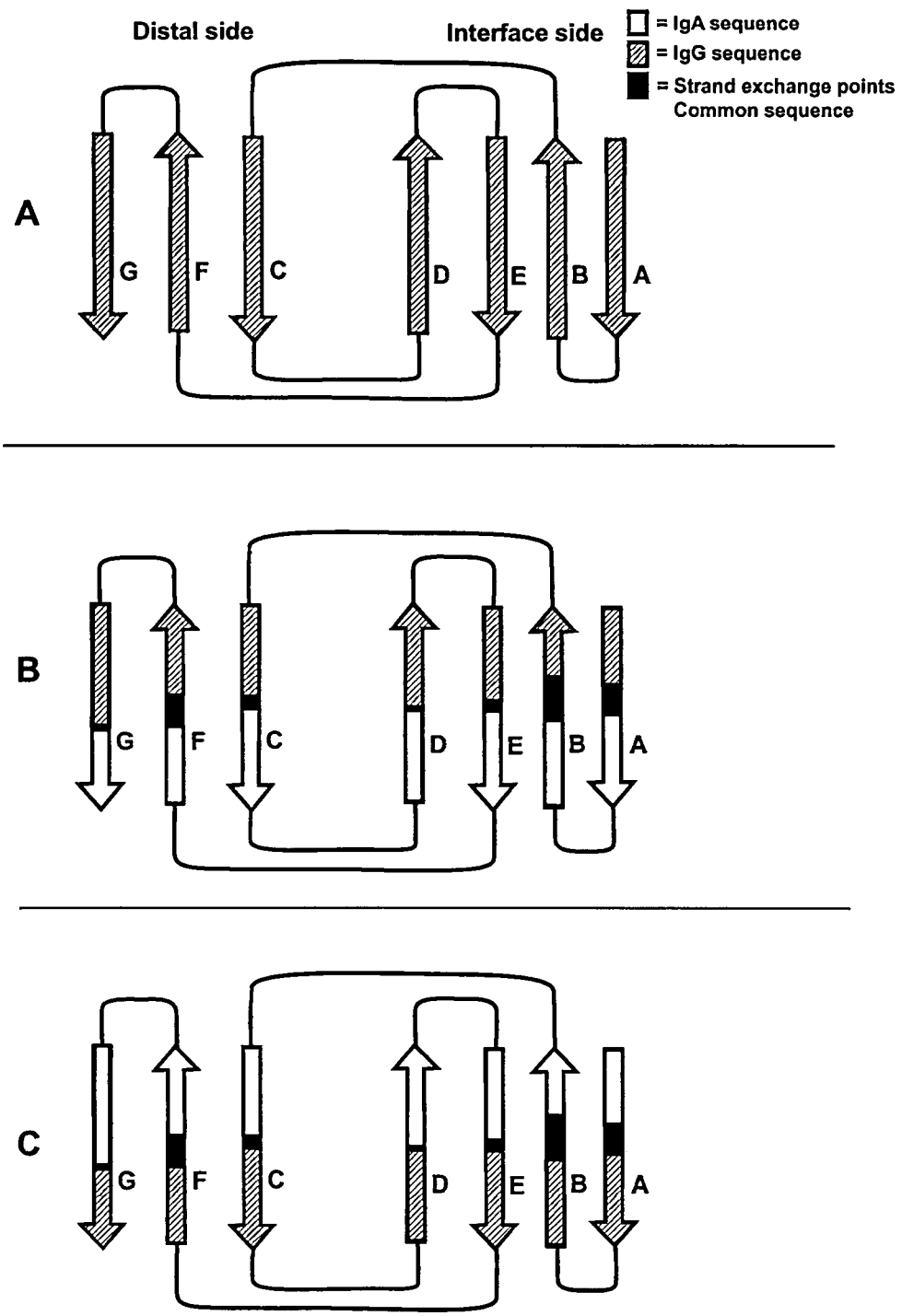
FIGS. 6A-C are schematic representations of the secondary structure of IgG CH3 and the two CH3-based SEEDs.
Figure 7:
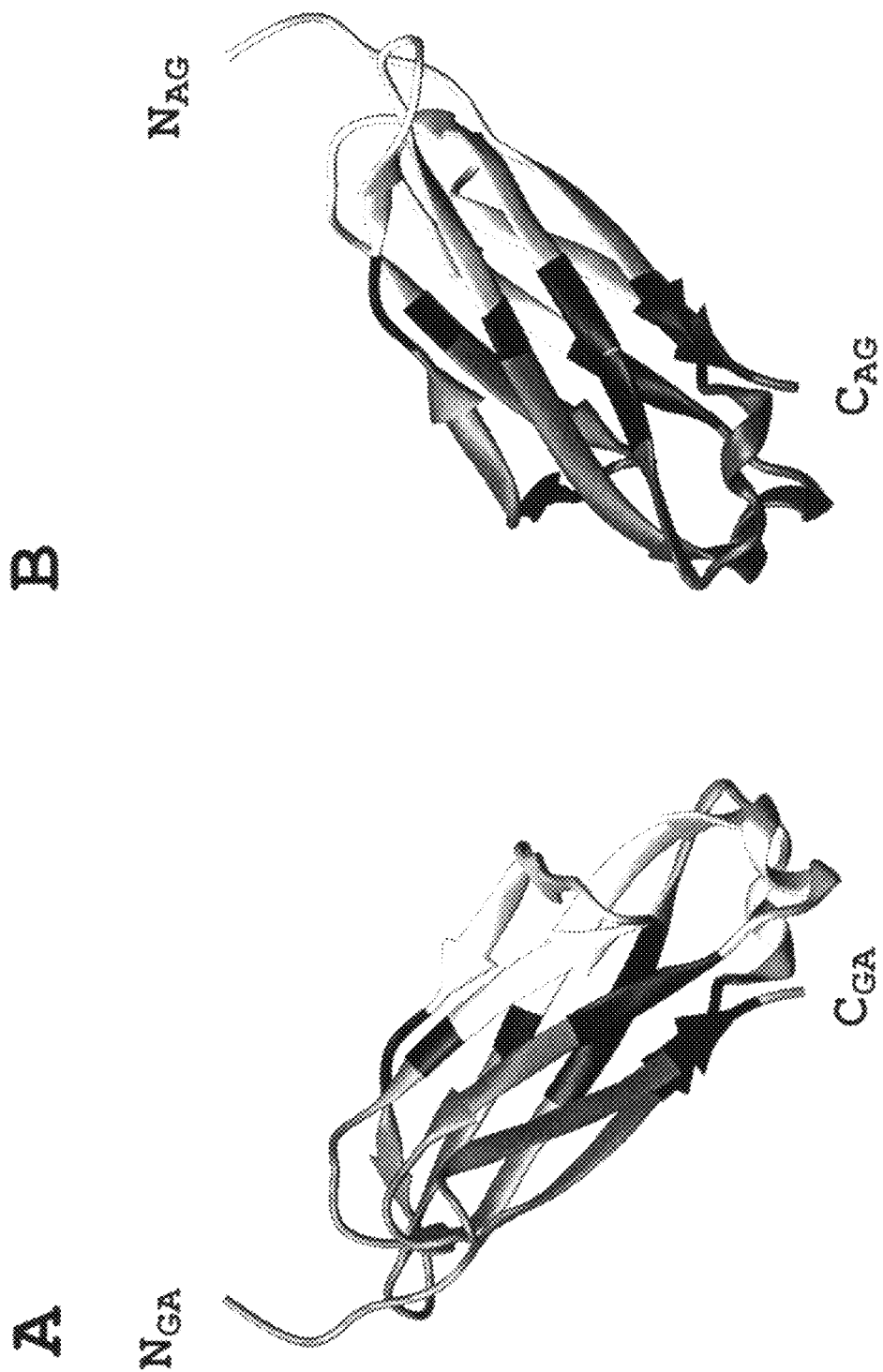
FIGS. 7A-C are ribbon diagram representations of the three-dimensional structure of the "GA SEED" and "AG SEED" CH3 domains and of their putative heterodimeric structure depicting exchange crossover point and CH3 domain interactions. In all diagrams, white or light gray ribbons represent IgA sequence and structure, dark gray corresponds to IgG sequence and structure, and black sections denote where the sequence exchanges from G to A or vice versa. Aside from the two exchange points at 55-56 and 101-102 (numbered according to FIG. 3B), all black residues are shared by IgA and IgG, in sequence and in basic structure.

Once the structural alignment is determined and the interface residues identified, the exchange points are ready to be chosen for creating the SEEDs. The CH3 homodimer has 180° rotational symmetry around an axis that runs between the domains approximately perpendicular to the beta strands (FIG. 4). Each domain has the N-terminus and C-terminus on opposite sides of the axis of symmetry. Therefore, CH3 domains dimerize in a hand-shaking manner, where only in a line down the center of the interface along the symmetry axis do residues on one side contact the same residue in the other partner. Residues on either side of that line contact the partner domain in opposite fashion: e.g., residues on the N-terminal side of the first domain make contact with residues in the second domain that are on the C-terminal side, and vice versa.

In one embodiment, a CH3-based SEED is designed to break the symmetry, making the two sides different. For example, strand exchange will make one side of the dimer more like IgA1, and the other side more like IgG. This approach creates two different CH3-based SEEDs that are approximately complementary in their use of IgG and IgA-derived amino acids. As shown in FIGS. 3A and 3B, the linear polypeptide sequence runs back and forth between IgG and IgA sequences in order to make one physical side of the dimeric structure IgA-like and the other side IgG-like. Thus, each final SEED sequence contains multiple exchange points, at each of which the linear sequence changes from IgA to IgG or from IgG to IgA (FIGS. 3A and 3B).

In general, there are many potential multiple exchange points in the polypeptide sequence that can be chosen to alternate between IgA and IgG1 sequences. An important consideration is that the final structure should have good structural characteristics (e.g., stability, folding, expression, homology to the original). This can be achieved by inspection, simple modeling, extensive calculation, trial and error, selection, or by other means. In the specific embodiment described here, the sequence homology between the CH3 domains of IgA and IgG1 was used to decide the exchange points. Alignment of the crystal structures of the IgG1 and IgA CH3 revealed approximately parallel lines of amino acids along an approximate plane angled across the middle of the domain. The residues on the plane were identical in both CH3 classes in all but two strands in the IgG1/IgA structural alignment. Furthermore, the structure alignment generally showed the side chains of those amino acids in the same rotamer orientations, particularly in the hydrophobic core. It was therefore hypothesized that these residues could be used as exchange points, and the residues on one or the other side could be altered without disrupting the overall structure. FIGS. 3A and 3B show the sequence alignment with the exchange points highlighted in bold letters. FIGS. 5 and 6A-C show the molecular structure illustrating the 3-dimensional locations of the exchange points.

In the two cases where the residues are not the same at a junction region, the choices of exchange points were based on structural considerations. In one instance, Pro395 and Pro396 in IgG1 correspond structurally to Ala399 and Ser400 in IgA1. The division was made between these two residues. The other location is near the C-terminus, Leu441 and Ser442 in IgG1 correspond structurally to Ile448 and Asp449 in IgA1. Again the division was made between these residues.

Protein-protein interactions are mediated by the complementarity of the two interacting surfaces. The dominant factor for the interaction is the composition and shape of those surfaces. Since the underlying backbone structures and hydrophobic interiors of the CH3 domains of IgA and IgG1 are similar, it was contemplated according to the principles of the invention that only the surface would have to be altered, while the rest of the domain could contain IgG sequences. In this case, the exchange points were designed on the strands that form the interface and were very close to one another, allowing only the residues critical for dimerization to be exchanged. Thus, as an alternative, it is possible that the rest of the structure could help stabilize the assembly domain, and so CH3 SEEDs with a single exchange point in each of the seven strands could have advantages.

Therefore, two types of SEEDs can be designed and designated as “Full” for the SEEDs in which most or all of the residues in the domain were involved in the strand exchange (corresponding to FIG. 1A) or “Surface” for the SEEDs in which the only altered residues are at the CH3 dimerization interface (corresponding to FIG. 1B).

Based on this Example, it will be appreciated by those skilled in the art that a variety of strategies can be used to generate SEEDs based on immunoglobulin superfamily constant domains.

Example 3

Designing the Sequences of the “Full” AG and GA SEEDs

As an example, the simplest way to make a “Full” SEED would be to use pure IgA sequence on the first side of the exchange point, and pure IgG1 sequence on the second side of the exchange point. If the exchange point is properly chosen, this would result in a SEED that should fold properly and would have an IgA1-like dimerizing surface on one side (e.g., approximately half) of the domain, and an IgG-like dimerizing surface on the other side. A ‘mirror image’ SEED can be made similarly, in which the first side is composed of IgG1 sequence and the second side is composed of IgA sequence. When these two SEEDs are expressed together, they will preferentially form heterodimers because only in the heterodimer will each surface be contacting a surface on the other domain that matches its class: that is, the first half of the first SEED, which is IgA1-like, will contact the second half of the second SEED, which is also IgA1-like, while the second half of the first SEED, which is IgG1-like, will contact the first half of the second SEED, which is also IgG1-like. Since both sides of the contact surface are highly complementary, the association should be strong. On the other hand, when either SEED attempts to form a homodimer, each half of the dimerization surface will contact a surface on the partner SEED that comes from a different class: that is, the first half of one SEED, which is IgA-like, will contact the second half of the partner domain, which is IgG-like; and the second half of the first SEED, which is IgG1-like, will contact the first half of the partner domain, which is IgA-like. Since these surfaces are not highly complementary, their affinity will be diminished, resulting in thermodynamics favoring the formation of fewer homodimers and more heterodimers.

In this example, the CH3 is the only part of the Fc or antibody that was altered. The rest of the Fc or immunoglobulin is from human IgG1. Altering the amino acid sequence where the CH3 contacts or interacts with CH2 could potentially create problems with the interface between the CH3 SEEDs and the IgG1 CH2 domains. In addition, this interface contains the binding site for FcRn, which confers important properties to the Fc that are desirable to retain. Therefore, structural information (Martin et al. (2001) *Molec. Cell* 7:867) was used to identify the CH3 residues involved in the interactions between CH3 and CH2, and between Fc and FcRn. Human IgG1 sequences were used for those residues in all SEEDs. Molecular modeling was also used to help choose the neighboring residues to avoid altering the structure of the FcRn interaction surface. The portion of CH3 that interacts with CH2 and with FcRn is not part of the dimerization interface, therefore, these alterations were unlikely to hinder the formation of heterodimers.

Figure 3A:
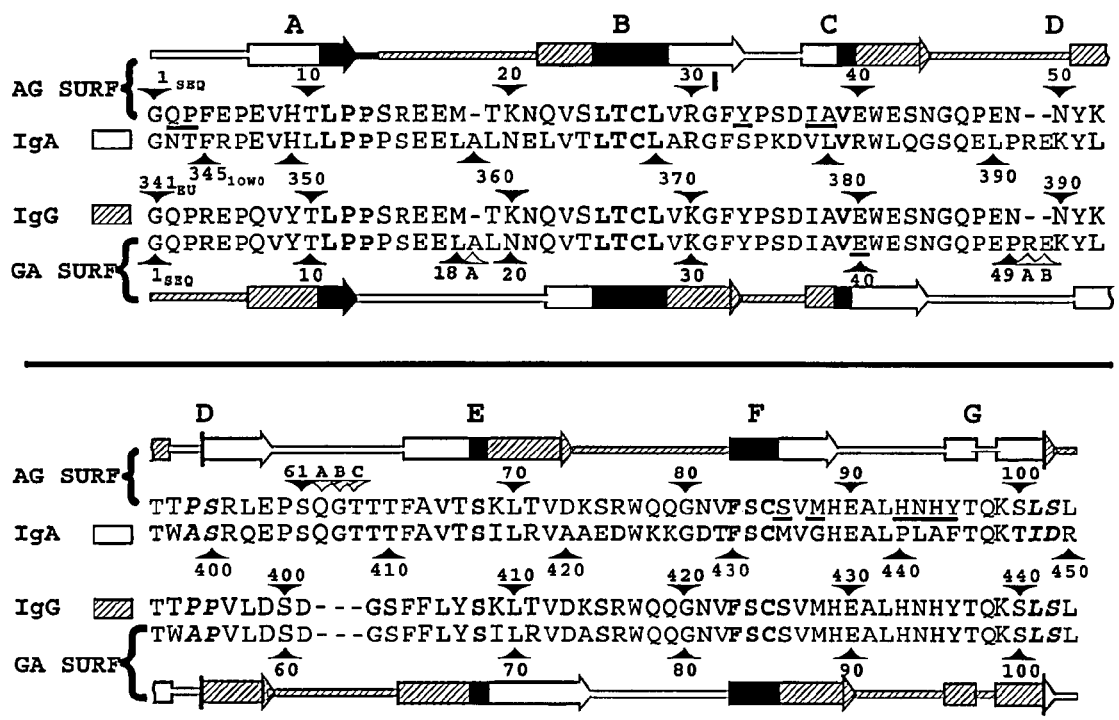
Figure 3B:
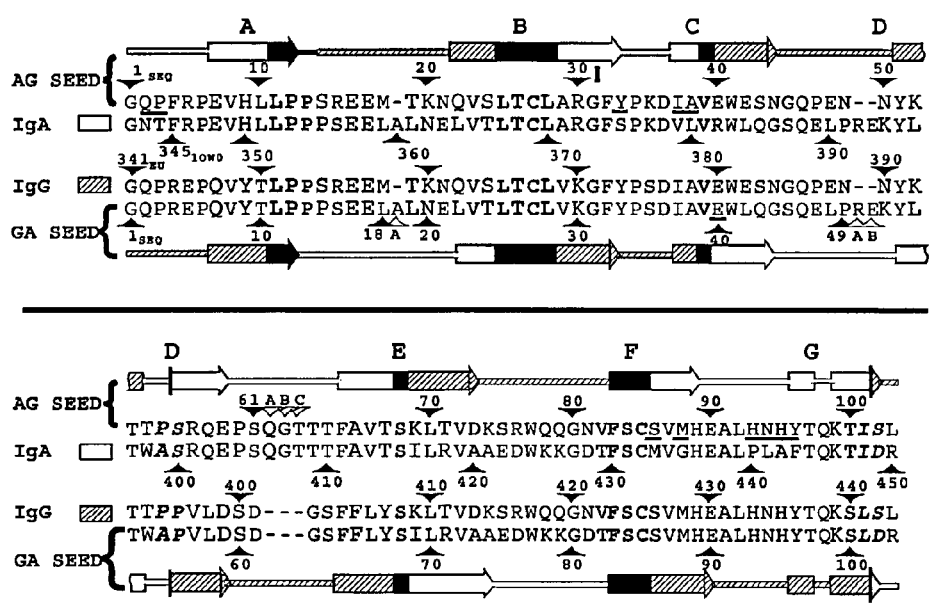
FIG. 3B depicts the sequence alignments and secondary structure of human IgA, IgG1 and daughter "Full" SEED sequences "AG SEED" (SEQ ID NO:3) and "GA SEED" (SEQ ID NO:6). IgG1 is numbered according to Kabat EU numbering, while IgA is sequentially numbered as in the PDB structure 1OW0 (native numbers in center of alignment). For the purposes of this figure, the sequential numbering of the SEED sequence is interrupted at extra loop residues, which are designated with letters "A", "B", etc. (e.g., 18A), to illustrate the structural alignment of the molecules. Strand exchange points are designated by bold sequence letters. The two exchange points that contain no common residues are italicized. Modeled secondary structures (arrows above and below sequences) of the two SEEDs illustrate the strand exchanges, and are colored to indicate the manner in which the domain was divided, as shown in FIGS. 6B and 6C. White segments □ are from IgA; gray segments ▓ are from IgG, and black segments ■ are common residues at exchange points. Twelve (12) residues in IgA segments are underlined. These are residues that were kept as IgG because of their proximity to the CH3/CH2 interface region. These residues are not involved in CH3 dimerization, but they are potentially important for the interaction with CH2, and/or with the complex with FcRn. Since the CH2 is human IgG for both SEEDs, these residues were kept to maintain both the native CH2/CH3 interaction and the various well-known advantages conferred by FcRn binding.

FIG. 3B has the "Full" SEED sequences aligned with the IgG1 and IgA sequences in structural alignment. Residues that reside at the exchange points are highlighted in bold. Residues that were unaltered due to their importance in maintaining the interaction with CH2 and/or with FcRn are underlined.

Example 4

Construction of Heterodimeric Fc and Antibody Molecules Containing CH3-Based SEEDs The following general approach was used to make HuFc and HuFc-IL2 constructs, as well as antibody and antibody-IL2 constructs, containing CH3 SEED domains in place of IgG1 CH3 domains. The CH3 domain of IgG1 is almost entirely contained in an approximately 0.4 kb Ngo MIV/Sma I genomic DNA fragment, which is present in pdCs or pdHL expression plasmids that express the constant region of an IgG1 heavy chain. Exemplary expression plasmids are, for example, pdCs-huFc-IL2 (see, for example, Lo et al., Protein Engineering [1998] 11:495), or pdHL7-KS-IL2 (see, for example U.S. Pat. No. 6,696,517). The Ngo MIV site lies within the intron sequence immediately 5' of the exon encoding IgG1 CH3, and the Sma I site lies in a sequence encoding $Ser_{444}Pro_{445}Gly_{446}$ near the C-terminus of IgG1 (Kabat EU Index). An exemplary DNA sequence of a mature human IgG1 Fc expressed from a pdCs vector is shown in SEQ ID NO:27. Replacement of the parental Ngo MIV/Sma I fragment with a Ngo MIV/Sma I fragment encoding a CH3 SEED of the invention generates upon expression a polypeptide containing a constant region with a CH3 SEED.

```
SEQ ID NO: 27
DNA sequence in pdCs encoding mature human IgG1 Fc
including terminal Lysine residue
GAGCCCAAATCTTCTGACAAAACTCACACATGCCCACCGTGCCCAGGTAA

GCCAGCCCAGGCCTCGCCCTCCAGCTCAAGGCGGGACAGGTGCCCTAGAG

TAGCCTGCATCCAGGGACAGGCCCCAGCCGGGTGCTGACACGTCCACCTC

CATCTCTTCCTCAGCACCTGAACTCCTGGGGGGACCGTCAGTCTTCCTCT

TCCCCCCAAAACCCAAGGACACCCTCATGATCTCCCGGACCCCTGAGGTC

ACATGCGTGGTGGTGGACGTGAGCCACGAAGACCCTGAGGTCAAGTTCAA

CTGGTACGTGGACGGCGTGGAGGTGCATAATGCCAAGACAAAGCCGCGGG

AGGAGCAGTACAACAGCACGTACCGTGTGGTCAGCGTCCTCACCGTCCTG

CACCAGGACTGGCTGAATGGCAAGGAGTACAAGTGCAAGGTCTCCAACAA

AGCCCTCCCAGCCCCCATCGAGAAAACCATCTCCAAAGCCAAAGGTGGGA

CCCGTGGGGTGCGAGGGCCACATGGACAGAGGCCGGCTCGGCCCACCCTC

TGCCCTGAGAGTGACCGCTGTACCAACCTCTGTCCCTACAGGGCAGCCCC

GAGAACCACAGGTGTACACCCTGCCCCCATCACGGGAGGAGATGACCAAG

AACCAGGTCAGCCTGACCTGCCTGGTCAAAGGCTTCTATCCCAGCGACAT

CGCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTC

ACCGTGGACAAGAGCAGGTGGCAGCAGGGGAACGTCTTCTCATGCTCCGT

GATGCATGAGGCTCTGCACAACCACTACACGCAGAAGAGCCTCTCCCTGT

CCCCGGGTAAATGA
```

Standard techniques were used to obtain DNA sequences encoding the CH3 SEEDs of the invention. For example, DNA molecules with following sequences as shown in SEQ ID NO:28, SEQ ID NO:29, SEQ ID NO:30, SEQ ID NO:31, SEQ ID NO:32, and SEQ ID NO:53 were synthesized de novo and propagated in a pUC-derived carrier plasmid (Blue Heron Biotechnology, Bothell, Wash.).

```
SEQ ID NO: 28
DNA fragment Ngo MIV/Sma I, containing sequence encoding AG(f0) SEED
(underlined corresponding to FIG. 3B, "Full AG SEED"):
gccggctcggcccaccctctgccctgagagtgaccgctgtaccaacctctgtccctacaGGGCAGCCCTTCCGGCCAGA

GGTCCACCTGCTGCCCCCATCACGGGAGGAGATGACCAAGAACCAGGTCAGCCTGA

CCTGCCTGGCACGCGGCTTCTATCCCAAGGACATCGCCGTGGAGTGGGAGAGCAAT

GGGCAGCCGGAGAACAACTACAAGACCACGCCTTCCCGGCAGGAGCCCAGCCAGG
```

GCACCACCACCTTCGCTGTGACCTCGAAGCTCACCGTGGACAAGAGCAGATGGCAG

CAGGGGAACGTCTTCTCATGCTCCGTGATGCATGAGGCTCTGCACAACCACTACACG

CAGAAGACCATCTCCCTGtccccggg

SEQ ID NO: 29
DNA fragment Ngo MIV/Sma I, containing sequence encoding AG(s0) SEED
(underlined corresponding to FIG. 3A, "Surface AG SEED"):
gccggctcggcccaccctctgccctgagagtgaccgctgtaccaacctctgtccctacaGGGCAGCCCTTCGAACCAGA

GGTCCACACCCTGCCCCCATCACGGGAGGAGATGACCAAGAACCAGGTCAGCCTGA

CCTGCCTGGTCCGCGGCTTCTATCCCAGCGACATCGCCGTGGAGTGGGAGAGCAATG

GGCAGCCGGAGAACAACTACAAGACCACGCCTTCCCGGCTGGAGCCCAGCCAGGGC

ACCACCACCTTCGCTGTGACCTCGAAGCTCACCGTGGACAAGAGCAGATGGCAGCA

GGGGAACGTCTTCTCATGCTCCGTGATGCATGAGGCTCTGCACAACCACTACACGCA

GAAGAGCCTCTCCCTGtccccggg

SEQ ID NO: 30
DNA fragment Ngo MIV/Sma I, containing sequence encoding GA(f0) SEED
(underlined corresponding to FIG. 3B, "Full GA SEED"):
gccggctcggcccaccctctgccctgagagtgaccgctgtaccaacctctgtccctacaGGGCAGCCCCGAGAACCAC

AGGTGTACACCCTGCCCCCACCGTCGGAGGAGCTGGCCCTGAACGAGCTGGTGACG

CTGACCTGCCTGGTCAAAGGCTTCTATCCCAGCGACATCGCCGTGGAGTGGCTGCAG

GGGTCCCAGGAGCTGCCCCGCGAGAAGTACCTGACTTGGGCACCCGTGCTGGACTC

CGACGGCTCCTTCTTCCTCTATAGTATACTGCGCGTGGCAGCCGAGGACTGGAAGAA

GGGGGACACCTTCTCATGCTCCGTGATGCATGAGGCTCTGCACAACCACTACACGCA

GAAGAGCCTCGACCGCtccccggg

SEQ ID NO: 31
DNA fragment Ngo MIV/Sma I, containing sequence encoding GA(s0) SEED
(underlined corresponding to FIG. 3A, "Surface GA SEED"):
gccggctcggcccaccctctgccctgagagtgaccgctgtaccaacctctgtccctacaGGGCAGCCCCGAGAACCAC

AGGTGTACACCCTGCCCCCACCGTCGGAGGAGCTGGCCCTGAACAACCAGGTGACG

CTGACCTGCCTGGTCAAAGGCTTCTATCCCAGCGACATCGCCGTGGAGTGGGAGAG

CAATGGGCAGCCGGAGCCCCGCGAGAAGTACCTGACTTGGGCACCCGTGCTGGACT

CCGACGGCTCCTTCTTCCTCTATTCGATACTGCGCGTGGACGCAAGCAGGTGGCAGC

AGGGGAACGTCTTCTCATGCTCCGTGATGCATGAGGCTCTGCACAACCACTACACGC

AGAAGAGCCTCTCCCTGtccccggg

SEQ ID NO: 32
DNA fragment Ngo MIV/Sma I, containing sequence encoding GA(f1) SEED
(underlined):
gccggctcggcccaccctctgccctgagagtgaccgctgtaccaacctctgtccctacaGGGCAGCCCCGAGAACCAC AGGTGTACACCCTGCCCCCACCGTCGGAGGAGCTGGCCCTGAACGAGCaGGTGACG

CTGACCTGCCTGGTCAAAGGCTTCTATCCCAGCGACATCGCCGTGGAGTGGCTGCAG

GGGTCCCAGGAGCTGCCCCGCGAGAAGTACCTGACTTGGaCcCCCGTGgTGGACTCC

GACGGCTCCTTCTTCCTCTATAGTATACTGCGCGTGaCAGCCGAtGACTGGAAGAAGG

GGGACACCTTCTCATGCTCCGTGATGCATGAGGCTCTGCACAACCACTACACGCAGA

AGAGCCTCGACCGCtccccggg

SEQ ID NO: 53
DNA fragment Ngo MIV/Sma I, containing sequence encoding GA(f2) SEED
(underlined):
gccggctcggcccaccctctgccctgagagtgaccgctgtaccaacctctgtccctacaGGGCAGCCCCGAGAACCAC AGGTGTACACCCTGCCCCCACCGTCGGAGGAGCTGGCCCTGAACGAGCaGGTGACG -continued

CTGACCTGCCTGGTCAAAGGCTTCTATCCCAGCGACATCGCCGTGGAGTGGCTGCAG

GGGTCCCAGGAGCTGCCCCGCGAGAAGTACCTGACTTGGgCaCCCGTGgacGACTCCG

ACGGCTCCcaCTTCCTCTATAGTATACTGCGCGTGaCAGCCGAtGACTGGAAGAAGGG

GGACACCTTCTCATGCTCCGTGATGCATGAGGCTCTGCACAACCACTACACGCAGAA

GAGCCTCGACCGCtccccggg

In addition, a polypeptide containing GA(f3) SEED may be encoded by the following DNA sequence:

```
SEQ ID NO: 54
DNA fragment Ngo MIV/Sma I, containing sequence encoding GA(f3) SEED
(underlined):
gccggctcggcccaccctctgccctgagagtgaccgctgtaccaacctctgtccctacaGGGCAGCCCCGAGAACCAC
```

AGGTGTACACCCTGCCCCCACCGTCGGAGGAGCTGGCCCTGAACGAGCaGGTGACG

CTGACCTGCCTGGTCAAAGGCTTCTATCCCAGCGACATCGCCGTGGAGTGGCTGCAG

GGGTCCCAGGAGCTGCCCCGCGAGAAGTACCTGACTTGGaCcCCCGTGaccGACTCCG

ACGGCTCCgacTTCCTCTATAGTATACTGCGCGTGaCAGCCGAtGACTGGAAGAAGGG

GGACACCTTCTCATGCTCCGTGATGCATGAGGCTCTGCACAACCACTACACGCAGAA

GAGCCTCGACCGCtccccggg

These synthetic sequences were additionally extended at their 3' end with an approximately 50 bp stretch of random DNA so as to allow easy separation of excised Ngo MIV/Sma I desired insert fragment and a similarly sized plasmid vector fragment during fragment purification. The gel purified Ngo MIV/Sma I fragments were then ligated to a similarly treated pdCs vector containing either an Fc moiety or an Fc-IL2 moiety, or alternatively, to a similarly treated pdHL vector containing either a DI-KS or a DI-KS-IL2 moiety. Thus, for example, pdCs-HuFc(AG(f0))-IL2, containing the Ngo MIV/Sma I fragment for AG(f0) SEED (SEQ ID NO:28), and pdCs-HuFc(GA(f0)), containing the Ngo MIV/Sma I fragment for GA(f0) SEED (SEQ ID NO:30), were obtained. pdCs-HuFc(AG(f0))-IL2 and pdCs-HuFc(GA(f0)) encode an Fc(AG(f0) SEED)-IL-2 polypeptide chain and an Fc(GA(f0) SEED) polypeptide chain, respectively. Exemplary sequences of Fc(AG(f0) SEED)-IL-2 and of Fc(GA(f0) SEED) are shown as SEQ ID NO:33 and SEQ ID NO:34, respectively, below. A diagram of the resulting heterodimeric protein is shown in FIG. 11A. To obtain simultaneous expression of both polypeptide chains from a host cell, the transcription units for these Fc polypeptides were combined on a single expression vector as described below in Example 5.

```
SEQ ID NO: 33
Polypeptide sequence of a Fc(AG(f0) SEED)-IL2:
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPFRPEVHLLPPSREEMTKNQVSLTCLARGFYPKDIAVEWESNGQPENNYK

TTPSRQEPSQGTTTFAVTSKLTVDKSRWQQGNVFSCSVMHEALHNHYTQKTISLSPGKA

PTSSSTKKTQLQLEHLLLDLQMILNGINNYKNPKLTRMLTFKFYMPKKATELKHLQCLE

EELKPLEEVLNLAQSKNFHLRPRDLISNINVIVLELKGSETTFMCEYADETATIVEFLNRW

ITFCQSIISTLT

SEQ ID NO: 34
Polypeptide sequence of a Fc(GA(f0) SEED):
EPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPPSEELALNELVTLTCLVKGFYPSDIAVEWLQGSQELPREK

YLTWAPVLDSDGSFFLYSILRVAAEDWKKGDTFSCSVMHEALHNHYTQKSLDRSPGK
```

Similarly, pdHL-DI-KS(AG(f0))-IL2, containing the Ngo MIV/Sma I fragment for AG(f0) SEED (SEQ ID NO:28), and pdHL-DI-KS(GA(f0)), containing the Ngo MIV/Sma I fragment for GA(f0) SEED (SEQ ID NO:30), were obtained. pdHL-DI-KS(AG(f0))-IL2 and pdHL-DI-KS(GA(f0)) encode DI-KS(AG(f0) SEED)-IL-2 heavy chain (SEQ ID NO:35), DI-KS(GA(f0) SEED) heavy chain (SEQ ID NO:36), respectively. Both expression vectors also encode the DI-KS light chain (SEQ ID NO:37).

SEQ ID NO: 35
Polypeptide sequence of DI-KS(AG(f0) SEED)-IL2 heavy chain:
QIQLVQSGPELKKPGSSVKISCKASGYTFTNYGMNWVRQAPGKGLKWMGWINTYTGEP

TYADDFKGRFTITAETSTSTLYLQLNNLRSEDTATYFCVRFISKGDYWGQGTTVTVSSAS

TKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKRVEPKSCDKTHTCPPCPAPELLGGPS

VFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPFRPEVHLLPPSRE

EMTKNQVSLTCLARGFYPKDIAVEWESNGQPENNYKTTPSRQEPSQGTTTFAVTSKLTV

DKSRWQQGNVFSCSVMHEALHNHYTQKTISLSPGAAPTSSSTKKTQLQLEHLLLDLQMI

LNGINNYKNPKLTRMLTFKFYMPKKATELKHLQCLEEELKPLEEVLNLAQSKNFHLRPR

DLISNINVIVLELKGSETTFMCEYADETATIVEFLNRWITFCQSIISTLT

SEQ ID NO: 36
Polypeptide sequence of DI-KS(GA(f0) SEED) heavy chain:
QIQLVQSGPELKKPGSSVKISCKASGYTFTNYGMNWVRQAPGKGLKWMGWINTYTGEP

TYADDFKGRFTITAETSTSTLYLQLNNLRSEDTATYFCVRFISKGDYWGQGTTVTVSSAS

TKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKRVEPKSCDKTHTCPPCPAPELLGGPS

VFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPPSE

ELALNELVTLTCLVKGFYPSDIAVEWLQGSQELPREKYLTWAPVLDSDGSFFLYSILRVA

AEDWKKGDTFSCSVMHEALHNHYTQKSLDRSPGK

SEQ ID NO: 37
Polypeptide sequence of DI-KS light chain:
QIVLTQSPASLAVSPGQRATITCSASSSVSYILWYQQKPGQPPKPWIFDTSNLASGFPSRFS

GSGSGTSYTLTINSLEAEDAATYYCHQRSGYPYTFGGGTKVEIKRTVAAPSVFIFPPSDEQ

LKSGTASVVCLLNNFYPREAKVQWKVDNALQSGNSQESVTEQDSKDSTYSLSSTLTLSK

ADYEKHKVYACEVTHQGLSSPVTKSFNRGEC

To obtain a single expression vector expressing both DI-KS(AG(f0) SEED)-IL-2 and DI-KS(GA(f0) SEED) heavy chain transcription units as well as the common light chain transcription unit, a construct was prepared essentially as follows: an approximately 3.9 kb Sal I/Mfe I fragment containing the sequence encoding KS(AG(f0) SEED)-IL-2 was excised from the pdHL-10 expression construct (pdHL-10 is a later generation pdHL expression vector containing a single Sal I site outside of the transcription unit) and ligated into a Sal I/Bam HI digested pBS plasmid, together with a Bam HI/Mfe I duplex linker fragment. This duplex linker fragment is composed of Oligo11 (SEQ ID NO:38) and Oligo12 (SEQ ID NO:39) and contains an internal Sal I site.

```
Oligo11 (SEQ ID NO: 38)
AATTGCCGGGTCGACATACG

Oligo12 (SEQ ID NO: 39)
GATCCGTATGTCGACCCGGC
```

The 3.9 kb fragment was then excised from pBS as a Sal I fragment and inserted into the unique Sal I site of a pdHL-10 expression construct already containing the transcription units encoding DI-KS(GA(f0) SEED) heavy chain and the DI-KS light chain.

Example 5

Assay to Determine Heterodimeric Fc Molecules Containing CH3-Based SEEDs

The examples described here involve CH3 dimerization, which is an important step in nucleating the formation of Fc and immunoglobulin heavy chain dimers. In theory, if two distinct Fc moieties (e.g., termed A and B) containing CH3 domains are expressed simultaneously in a cell, they could pair and form Fc dimeric molecules in the following configurations: A:A, A:B, and B:B. If the CH3 domains and hinge domains are identical, the configurations A:A, A:B, and B:B are expected to occur in a 1:2:1 ratio if A and B are expressed in equal amounts. The relative amounts, the kinetics and thermodynamics of A-A, A-B, and B-B interactions are important governing factors for the observed ratio of these three final species, as would the expression levels. In general, when protein A and protein B are expressed in relative amounts [A] and [B], where [A]+[B]=1, and homodimers and heterodimers are produced in relative concentrations [A-A], [A-B], and [B-B], if there is unbiased association, these dimeric species will respectively be present in a ratio of $[A]^2:2*[A][B]:[B]^2$. If the relative concentration [A–B]>2*[A][B], then heterodimerization is favored, while if the relative concentration [A−B]<2*[A][B], then homodimerization is favored. For a preferred SEED pair, the ratio [A−B]/2*[A][B] is greater than 2, and preferably greater than 3, and more preferably greater than 5.

To determine the ratios of the different species, one needs a way to distinguish them by an assay. An easy way to do this is to attach a fusion partner to one of the Fc subunits (e.g., "A"), which would result in each of the three final species having a significantly different molecular weight. Accordingly, constructs were prepared to express both human Fc (HuFc) and human Fc fused to human IL-2 (HuFc-IL-2) in one cell. The constructs were prepared as follows: The gene for HuFc was excised from a vector containing an Fc moiety (see, for example, Lo et al., Protein Engineering [1998] 11:495) by enzymatic restriction at a 5' XbaI site and a 3' XhoI site. The 1.4 Kb fragment containing the HuFc gene was gel purified and subcloned into a second vector, pdCS-MuFc-KS-kappa, replacing its muFc with HuFc. The HuFc gene was flanked by two SalI sites outside the promoter region.

A third vector containing a gene coding for HuFc-IL-2 and a single SalI site was chosen to receive the HuFc gene. The vector was cut with SalI, treated with Calf Intestinal Phosphatase (CIP) and gel purified. The second vector was digested with SalI and a 2.5 Kb fragment was gel purified. This fragment contained the HuFc gene and a promoter, and was inserted into the gel-purified third vector. The final resulting vector contained two different transcription units with duplicated versions of the same regulatory elements, one transcription unit controlling the expression of wild type HuFc and the other controlling the expression of wild type HuFc-IL-2. Expression constructs containing SEED-based HuFc and SEED-based HuFc-IL-2 were similarly made.

This final vector was expanded using Qiagen® maxi-prep. 10 mg of the DNA was used to transiently transfect baby hamster kidney (BHK) cells, using the Lipofectamine™ 2000 kit (Invitrogen). Cells were split, half grown in regular medium, the other half in serum-free medium, for two days. Supernatants (e.g., 100 ul) were harvested. 10 microliters of protein-A beads were added and mixed overnight at 4° C. to bind the protein. After washing 3× with PBS containing 1% Triton®-X100, samples were loaded onto Nu-Page® (Invitrogen) 4-12% gradient Bis-Tris gels, under both reducing and non-reducing conditions. Gels were stained with colloidal blue (Invitrogen) for direct protein visualization.

Typical control results are shown in lanes 8-10 in the gels shown in FIG. 12. The reducing gel in FIG. 12C shows the ratio of HuFc and HuFc-IL-2 subunits. The non-reducing gel in FIG. 12B shows that the HuFc and HuFc-IL2 molecules dimerize randomly, with no preference for heterodimerization as compared to homodimerization.

Gels were also transferred to nitrocellulose membranes for Western blot analysis. In the Western blots, protein was detected in two ways in order to measure both the Fc and the IL-2. Antibodies against human IgG Fc (Jackson Immunolabs) conjugated to horseradish peroxidase (HRP) were used to detect Fc. The blots were detected with ECL substrate and film exposure. A biotinylated antibody against human IL-2 (R&D systems) was used to detect IL-2, and the signal was developed by adding avidin conjugated to HRP, and detecting with ECL substrate and film exposure. These experiments confirmed the identity of bands shown in FIG. 12.

To measure the levels of heterodimers and homodimers formed during expression of "Full" GA SEED/AG SEED and "Surface" GA SEED/AG SEED proteins, similar experiments were performed. Single expression vector constructs expressing an AG SEED-IL2 fusion protein and a GA SEED protein were constructed as described above for the expression of Fc/Fc-IL2. As shown in lanes 2-4 in FIGS. 12B and 12C, when the "Full" GA SEED (Fc(GA(f0) SEED) and the "Full" AG SEED-IL-2 (Fc(AG(f0) SEED)-IL2) proteins were co-expressed in NS/0 cells, heterodimerization was strongly preferred, with no detectable Fc(AG SEED)-IL2 homodimers, and only very small amounts of the Fc(GA SEED) homodimers were detected. Similarly, as shown in lanes 5-7 in FIGS. 12B and 12C, when the "Surface" GA SEED (Fc(GA(s0) SEED) and the "Surface" AG SEED-IL-2 (Fc(AG(s0) SEED)-IL2) proteins were co-expressed in NS/0 cells, heterodimerization was strongly favored, with no detectable Fc(AG SEED)-IL-2 homodimers, and only small amounts of the Fc(GA SEED) homodimer detected. It was estimated that heterodimers constituted about >90% of the total amount of the proteins assembled in the cell.

Example 6

Construction, Expression, and Heterodimerization Properties of Seed Molecules with Reduced Immunogenicity Because the AG and GA SEED protein sequences are hybrids between two different naturally occurring human sequences, these sequences include peptide segments that are not found in normal human proteins and that may be processed into non-self MHC Class II T cell epitopes. Therefore, the following sequences were designed to reduce the number of potential non-self T-cell epitopes in the AG SEED and GA SEED sequences, depicted by the polypeptide sequence shown in SEQ ID NO:1 and SEQ ID NO:2, respectively, wherein $X_1$, $X_2$, $X_3$, $X_4$, $X_5$, or $X_6$ may be any amino acid. In some embodiments, in SEQ ID NO:1, $X_1$ is S, $X_2$ is V or T, and $X_3$ is S. In some embodiments, in SEQ ID NO:2, $X_1$ is Q, $X_2$ is A or T, $X_3$ is L, V, D, or T, $X_4$ is F, A, D, E, G, H, K, N, P, Q, R, S, or T, $X_5$ is T, and $X_6$ is D.

```
SEQ ID NO: 1
Polypeptide sequence of AG SEED, with variant amino acids
X1-X3:
GQPFRPEVHLLPPSREEMTKNQVSLTCLARGFYPX1DIAVEWESNGQPENNYKTTPSRQE

PSQGTTTFAVTSKLTX2DKSRWQQGNVFSCSVMHEALHNHYTQKX3ISL

SEQ ID NO: 2
Polypeptide sequence of GA SEED, with variant amino acids
X1-X6:
GQPREPQVYTLPPPSEELALNEX1VTLTCLVKGFYPSDIAVEWLQGSQELPREKYLTWX2

PVX3DSDGSX4FLYSILRVX5AX6DWKKGDTFSCSVMHEALHNHYTQKSLDR
```

The DNA molecule (SEQ ID NO:32) encoding exemplary SEED variant GA(f1) SEED (SEQ ID NO:7) was made by de novo synthesis and was introduced into the pdCs expression vector as described in Example 4, producing the polypeptide Fc(GA(f1) SEED).

```
SEQ ID NO: 7
Polypeptide sequence of GA(f1) SEED:
GQPREPQVYTLPPPSEELALNEQVTLTCLVKGFYPSDIAVEWLQGSQELPREKYLTWTPV

VDSDGSFFLYSILRVTADDWKKGDTFSCSVMHEALHNHYTQKSLDR
```

Mutations were introduced into the exemplary variant SEED moieties, AG(f1) SEED (SEQ ID NO:4), AG(f2) SEED (SEQ ID NO:5), and GA(f2) SEED (SEQ ID NO:8), by a two-step PCR approach in which two mutagenized, partially overlapping PCR fragments from a first round of PCR amplification are combined in a second round of PCR amplification to generate the final full-length fragment, using standard methods familiar to those skilled in the art. Essentially, two PCR reactions were performed in the first round, each with a PCR primer incorporating the mutant sequence paired with an appropriate flanking primer containing suitable restriction sites, Ngo MIV for the upstream primer and Sma I for the downstream primer, and a DNA template encoding the appropriate parent SEED moiety. The same flanking PCR primers were used in the second PCR amplification reaction, using the products of the first PCR amplification as templates. The resultant fragment was cloned into a pCR®2.1 vector (Invitrogen) and its sequence was verified. Finally, the 0.4 kb Ngo MIV/Sma I DNA fragment was excised from the vector, gel purified, and ligated into a similarly treated recipient expression plasmid, as described in Example 4.

Specifically, for AG(f1) SEED, primer pairs Oligo1 (SEQ ID NO:40)/Oligo2 (SEQ ID NO:41) and Oligo3 (SEQ ID NO:42)/Oligo4 (SEQ ID NO:43) with template pdCs-Fc(AG (f0) SEED)-IL2 were used in the first round of PCR reactions. Oligo1 (SEQ ID NO:40)/Oligo4 (SEQ ID NO:43) were used in the second round of PCR reactions, generating the DNA fragment shown in SEQ ID NO:44 which was introduced into pdCs-Fc(AG(f0) SEED)-IL2. For AG(f1) SEED, primer pairs Oligo1 (SEQ ID NO:40)/Oligo5 (SEQ ID NO:45) and Oligo6 (SEQ ID NO:46)/Oligo4 (SEQ ID NO:43) with template pCR2.1 containing the sequence shown in SEQ ID NO:44 were used in the first round of PCR reactions. Oligo1 (SEQ ID NO:40)/Oligo4 (SEQ ID NO:43) were used in the second round of PCR reactions, generating the DNA fragment shown in SEQ ID NO:47 which was introduced into pdCs-Fc(AG (f0) SEED)-IL2. For GA(f2) SEED, primer pairs Oligo1 (SEQ ID NO:40)/Oligo10 (SEQ ID NO:48) and Oligo7 (SEQ ID NO:49)/Oligo9 (SEQ ID NO:50) with template carrier plasmid pUC containing the sequence shown in SEQ ID NO:32 were used in the first round of PCR reactions. Oligo1 (SEQ ID NO:40)/Oligo9 (SEQ ID NO:50) were used in the second round of PCR reactions, generating the DNA fragment shown in SEQ ID NO:47 which was introduced into pdCs-Fc(GA(f2) SEED). All the sequences referred to above are shown below.

```
Oligo1 (SEQ ID NO: 40)
GCCGGCTCGGCCCACCCTCT

Oligo2 (SEQ ID NO: 41)
CGGCGATGTCGCTGGGATAGAA

Oligo3 (SEQ ID NO: 42)
TTCTATCCCAGCGACATCGCCG

Oligo4 (SEQ ID NO: 43)
CCCGGGGACAGGGAGATGGACTTCTGCGTGT

Oligo5 (SEQ ID NO: 45)
GCTCTTGTCTGTGGTGAGCTT

Oligo6 (SEQ ID NO: 46)
AAGCTCACCACAGACAAGAGC

Oligo7 (SEQ ID NO: 49)
CCTGACTTGGGCACCCGTGGACGACTCCGACGGCTCCCACTTCCTCTATA

Oligo9 (SEQ ID NO: 50)
CCCGGGGAGCGGTCGAGGCTC

Oligo10 (SEQ ID NO: 48)
TATAGAGGAAGTGGGAGCCGTCGGAGTCGTCCACGGGTGCCCAAGTCAGG

SEQ ID NO: 44
DNA fragment Ngo MIV/Sma I, containing sequence encoding AG(f1) SEED
(underlined):
gccggctcggcccaccctctgccctgagagtgaccgctgtaccaacctctgtccctacaGGGCAGCCCTTCCGGCCAGA

GGTCCACCTGCTGCCCCCATCACGGGAGGAGATGACCAAGAACCAGGTCAGCCTGA

CCTGCCTGGCACGCGGCTTCTATCCCAgcGACATCGCCGTGGAGTGGGAGAGCAATG
```

```
GGCAGCCGGAGAACAACTACAAGACCACGCCTTCCCGGCAGGAGCCCAGCCAGGGC

ACCACCACCTTCGCTGTGACCTCGAAGCTCACCGTGGACAAGAGCAGATGGCAGCA

GGGGAACGTCTTCTCATGCTCCGTGATGCATGAGGCTCTGCACAACCACTACACGCA

GAAGtCCATCTCCCTGtccccggg

SEQ ID NO: 47
DNA fragment Ngo MIV/Sma I, containing sequence encoding AG(f2) SEED
(underlined):
gccggctcggcccaccctctgccctgagagtgaccgctgtaccaacctctgtccctacaGGGCAGCCCTTCCGGCCAGA

GGTCCACCTGCTGCCCCCATCACGGGAGGAGATGACCAAGAACCAGGTCAGCCTGA

CCTGCCTGGCACGCGGCTTCTATCCCAgcGACATCGCCGTGGAGTGGGAGAGCAATG

GGCAGCCGGAGAACAACTACAAGACCACGCCTTCCCGGCAGGAGCCCAGCCAGGGC

ACCACCACCTTCGCTGTGACCTCGAAGCTCACCacaGACAAGAGCAGATGGCAGCAG

GGGAACGTCTTCTCATGCTCCGTGATGCATGAGGCTCTGCACAACCACTACACGCAG

AAGtCCATCTCCCTGtccccggg
```

Fc(AG(f1) SEED), Fc(AG(f2) SEED), Fc(GA(f1) SEED)-IL2 and Fc(GA(f2) SEED)-IL2 sequences were expressed individually and in combinations in HEK 293T cells, and the resulting secreted proteins were partially purified based on Fc binding to Staphylococcus A protein and characterized by SDS-PAGE. When the samples were run on a reducing SDS gel, it was apparent that the Fc(AG(f1) SEED) and Fc(AG(f2) SEED) proteins were expressed very poorly by themselves, which is similar to the parent Fc(AG(f0) SEED) protein. Without wishing to be bound by theory, the poor expression most likely results from the proteolysis of the monomeric protein that has no dimerization partner. The Fc(GA(f1) SEED)-IL2 protein was expressed at high level, while the Fc(GA(f2) SEED)-IL2 protein, differing by the additional amino acid substitution Val75Thr, was expressed at a very low level. Again, without wishing to be bound by theory, the poor expression may result from the proteolysis of the monomeric protein that has no dimerization partner. The combinations Fc(AG(f1) SEED) plus Fc(GA(f1) SEED)-IL2, Fc(AG(f2) SEED) plus Fc(GA(f1) SEED)-IL2, Fc(AG(f1) SEED) plus Fc(GA(f2) SEED)-IL2, and Fc(AG(f2) SEED) plus Fc(GA(f2) SEED)-IL2, were tested and all were expressed at high levels. The same samples were run on a non-reducing gel and confirmed these results. This analysis indicated that, for the combinations, essentially all of the expressed protein was heterodimeric. These results indicate that certain variant GA and AG SEED proteins with reduced immunogenicity retain their preference for heterodimerization.

Example 7

Expression of an Antibody-Cytokine Fusion Protein Using Seed Fc Regions

To further demonstrate the versatility of the SEED-based Fc regions, an intact antibody with a single IL-2 moiety was constructed as described in Example 4. A diagram of this protein is shown in FIG. 11B. Specifically, the protein contained antibody V regions that bind to EpCAM and that have the sequences as described in U.S. Pat. No. 6,696,517, human IgG1 CH1 and CH2 domains, human Ckappa, the GA and AG SEED domains, and human IL-2 fused to the C-terminus of the AG SEED-containing heavy chain.

The protein was expressed in mammalian cells according to standard techniques producing a protein with the polypeptide chains shown in SEQ ID NO:37, SEQ ID NO:36, and SEQ ID NO:35.

The resulting protein was characterized to determine the extent to which heterodimeric forms were secreted from the mammalian cells. For example, the secreted protein was characterized by non-reducing SDS-polyacrylamide gel electrophoresis. In principle, three bands might be identified, corresponding to antibodies with no, one or two IL-2 moieties. The actual non-reducing gel showed predominantly a single band with a molecular weight corresponding to an antibody with a single IL-2 moiety. A much less intense band with a molecular weight corresponding to no IL-2 moieties was seen, and a band with a molecular weight corresponding to two IL-2 moieties was not detectable. When the samples were reduced before running on the gel, approximately equal amounts of protein corresponding to antibody heavy chain and heavy chain-IL2 were detected.

The foregoing description of the present invention provides illustration and description, but is not intended to be exhaustive or to limit the invention to the precise one disclosed. Modifications and variations consistent with the above teachings may be acquired from practice of the invention. Thus, it is noted that the scope of the invention is defined by the claims and their equivalents

INCORPORATION BY REFERENCE

All sequence and structure access numbers, publications and patent documents cited in this application are incorporated by reference in their entirety for all purposes to the same extent as if the contents of each individual publication or patent document were incorporated herein.

What is claimed is:

1. A heterodimeric fusion protein comprising first and second polypeptides, each comprising a CH3 domain mediating the heterodimerization of the first and second polypeptides, wherein each CH3 domain is a modified IgG CH3 domain substituted with corresponding amino acid residues from an IgA CH3 domain,
wherein each modified IgG CH3 domain comprises substitutions selected from the group consisting of: Glu at Kabat position 347, His at Kabat position 349, Pro at Kabat position 354, Leu at Kabat position 359, Asn at Kabat position 360, Leu at Kabat position 362, Thr at Kabat position 364, Arg at Kabat position 370, Lys at Kabat position 390, Leu at Kabat position 392, Trp at Kabat position 394, Ala at Kabat position 395, Arg at Kabat position 397, Glu at Kabat position 399, Pro at Kabat position 400, Ala at Kabat position 405, Thr at Kabat position 407, Ile at Kabat position 409, and Arg at Kabat position 411;
wherein the substitutions in the first and second polypeptides occur at different positions; and
wherein heterodimerization of the modified IgG CH3 domains is enhanced compared to IgG CH3 domains without the substitutions.

2. The heterodimeric fusion protein of claim 1, wherein the first polypeptide comprises the amino acid sequence of SEQ ID NO: 10 and the second polypeptide comprises the amino acid sequence of SEQ ID NO: 11.

3. The heterodimeric fusion protein of claim 1, wherein the first polypeptide comprises the amino acid sequence of SEQ ID NO: 3 and the second polypeptide comprises the amino acid sequence of SEQ ID NO: 6.

4. The heterodimeric fusion protein of claim 1, wherein the first polypeptide comprises the amino acid sequence of SEQ ID NO: 5 and the second polypeptide comprises the amino acid sequence of SEQ ID NO: 8.

5. A heterodimeric fusion protein comprising first and second polypeptides, each comprising a CH3 domain mediating the heterodimerization of the first and second polypeptides, wherein each CH3 domain is a modified IgG CH3 domain substituted with corresponding amino acid residues from an IgA CH3 domain,
wherein each modified IgG CH3 domain comprises substitutions selected from the group consisting of: Glu at Kabat position 347, His at Kabat position 349, Pro at Kabat position 354, Leu at Kabat position 359, Asn at Kabat position 360, Leu at Kabat position 362, Thr at Kabat position 364, Arg at Kabat position 370, Lys at Kabat position 390, Leu at Kabat position 392, Trp at Kabat position 394, Ala at Kabat position 395, Arg at Kabat position 397, Glu at Kabat position 399, Pro at Kabat position 400, Thr at Kabat position 407, Ile at Kabat position 409, and Arg at Kabat position 411;
wherein the substitutions in the first and second polypeptides occur at different positions; and
wherein heterodimerization of the modified IgG CH3 domains is enhanced compared to IgG CH3 domains without the substitutions.

* * * * *